(12) United States Patent
Dorian et al.

(10) Patent No.: US 7,708,152 B2
(45) Date of Patent: May 4, 2010

(54) METHOD AND APPARATUS FOR PREPARING PLATELET RICH PLASMA AND CONCENTRATES THEREOF

(75) Inventors: Randel Dorian, San Diego, CA (US); Michael D. Leach, Warsaw, IN (US)

(73) Assignees: Hanuman LLC, San Francisco, CA (US); Biomet Biologics, LLC, Warsaw, IN (US)

( * ) Notice: Subject to any disclaimer, the term of this patent is extended or adjusted under 35 U.S.C. 154(b) by 406 days.

(21) Appl. No.: 11/342,761

(22) Filed: Jan. 30, 2006

(65) Prior Publication Data

US 2006/0175242 A1   Aug. 10, 2006

Related U.S. Application Data

(60) Provisional application No. 60/651,050, filed on Feb. 7, 2005, provisional application No. 60/654,718, filed on Feb. 17, 2005, provisional application No. 60/723,312, filed on Oct. 4, 2005.

(51) Int. Cl.
*B01D 21/26* (2006.01)
*B04B 7/08* (2006.01)

(52) U.S. Cl. ............. 210/512.3; 210/319; 210/294; 210/321.68; 210/321.87; 210/380.1; 210/787; 210/360.1; 210/512.1; 494/35; 494/37

(58) Field of Classification Search ............ 604/7, 604/507; 210/321, 789, 321.6, 321.67, 651, 210/360.1, 321.68

See application file for complete search history.

(56) References Cited

U.S. PATENT DOCUMENTS 2,553,004 A   5/1951   Rabatine (Continued)

FOREIGN PATENT DOCUMENTS

AU   696278   1/1999

(Continued)

OTHER PUBLICATIONS

Collier B. S. et al, The pH dependence of quantitative ristocetin-induced platelet aggregation—A new device for maintenance of platelet-rich plasma pH.

(Continued)

*Primary Examiner*—Krishnan S Menon
*Assistant Examiner*—Marjorie Christian
(74) *Attorney, Agent, or Firm*—Harness, Dickey

(57) ABSTRACT

The PRP separator-concentrator of this invention is suitable for office use or emergency use for trauma victims. The PRP separator comprises a motorized centrifugal separation assembly, and a concentrator assembly. The centrifugal separator assembly comprises a centrifugal drum separator that includes an erythrocyte capture module and a motor having a drive axis connected to the centrifugal drum separator. The concentrator assembly comprises a water-removal module for preparing PRP concentrate. The centrifugal drum separator has an erythrocyte trap. The water removal module can be a syringe device with water absorbing beads or it can be a pump-hollow fiber cartridge assembly. The hollow fibers are membranes with pores that allow the flow of water through the fiber membrane while excluding flow of clotting factors useful for sealing and adhering tissue and growth factors helpful for healing while avoiding activation of platelets and disruption of any trace erythrocytes present in the PRP.

12 Claims, 18 Drawing Sheets

U.S. PATENT DOCUMENTS

| | | |
|---|---|---|
| 3,141,846 A | 7/1964 | Laven, Jr. |
| 3,409,165 A | 11/1968 | Creith |
| 3,420,374 A | 1/1969 | Umeda |
| 3,441,143 A | 4/1969 | Kudlaty |
| 3,453,364 A | 7/1969 | Flodin et al. |
| 3,469,369 A | 9/1969 | Helmke |
| 3,508,653 A | 4/1970 | Coleman |
| 3,593,915 A | 7/1971 | Steinacker |
| 3,647,070 A | 3/1972 | Adler |
| 3,779,383 A | 12/1973 | Ayres |
| 3,785,549 A | 1/1974 | Lantham, Jr. |
| 3,814,248 A | 6/1974 | Lawhead |
| 3,850,369 A | 11/1974 | Bull et al. |
| 3,879,295 A | 4/1975 | Glover et al. |
| 3,894,952 A | 7/1975 | Ayres |
| 3,897,343 A | 7/1975 | Ayers |
| 3,909,419 A | 9/1975 | Ayers |
| 3,929,646 A | 12/1975 | Adler |
| 3,931,010 A | 1/1976 | Ayres |
| 3,931,018 A | 1/1976 | North, Jr. |
| 3,935,113 A | 1/1976 | Ayres |
| 3,941,699 A | 3/1976 | Ayres |
| 3,972,812 A | 8/1976 | Gresl, Jr. |
| 3,982,691 A | 9/1976 | Schultz |
| 4,001,122 A | 1/1977 | Griffin |
| 4,046,699 A | 9/1977 | Zine, Jr. |
| 4,055,501 A | 10/1977 | Cornell |
| 4,059,108 A | 11/1977 | Latham, Jr. |
| 4,077,396 A | 3/1978 | Wardlaw et al. |
| 4,152,270 A | 5/1979 | Cornell |
| 4,159,896 A | 7/1979 | Levine |
| 4,187,979 A | 2/1980 | Cullis et al. |
| 4,204,537 A | 5/1980 | Latham, Jr. |
| 4,225,580 A | 9/1980 | Rothman et al. |
| 4,229,298 A | 10/1980 | Bange |
| 4,269,718 A | 5/1981 | Persidsky |
| 4,294,707 A | 10/1981 | Ikeda et al. |
| 4,298,598 A | 11/1981 | Schwarz et al. |
| 4,300,717 A | 11/1981 | Latham, Jr. |
| 4,303,193 A | 12/1981 | Latham, Jr. |
| 4,314,823 A | 2/1982 | Rich, Jr. et al. |
| 4,322,298 A | 3/1982 | Persidsky |
| 4,332,351 A | 6/1982 | Kellogg et al. |
| 4,362,567 A | 12/1982 | Schwarz et al. |
| 4,364,832 A | 12/1982 | Ballies |
| 4,377,572 A | 3/1983 | Schwarz et al. |
| 4,414,976 A | 11/1983 | Schwarz et al. |
| 4,416,654 A | 11/1983 | Schoendorfer et al. |
| 4,417,981 A | 11/1983 | Nugent |
| 4,424,132 A | 1/1984 | Iriguchi et al. |
| 4,427,650 A | 1/1984 | Stroetmann et al. |
| 4,427,651 A | 1/1984 | Stroetmann et al. |
| 4,442,655 A | 4/1984 | Stroetmann et al. |
| 4,446,021 A | 5/1984 | Aufderhaar et al. |
| 4,453,939 A | 6/1984 | Zimmerman et al. |
| 4,464,167 A | 8/1984 | Schoendorfer et al. |
| 4,537,767 A | 8/1985 | Rothman et al. |
| RE32,089 E | 3/1986 | Blatt et al. |
| 4,610,656 A | 9/1986 | Mortensen |
| 4,617,009 A | 10/1986 | Ohlin et al. |
| 4,627,879 A | 12/1986 | Rose et al. |
| 4,631,055 A | 12/1986 | Redl et al. |
| 4,632,761 A | 12/1986 | Bowers et al. |
| 4,639,316 A | 1/1987 | Eldegheidy |
| 4,650,678 A | 3/1987 | Fuhge et al. |
| 4,655,211 A | 4/1987 | Sakamoto et al. |
| 4,672,969 A | 6/1987 | Dew |
| 4,675,117 A | 6/1987 | Neumann et al. |
| 4,680,025 A | 7/1987 | Kruger et al. |
| 4,714,457 A | 12/1987 | Alterbaum |
| 4,722,790 A | 2/1988 | Cawley et al. |
| 4,724,317 A | 2/1988 | Brown et al. |
| 4,735,616 A | 4/1988 | Eibl et al. |
| 4,735,726 A | 4/1988 | Duggins |
| 4,738,655 A * | 4/1988 | Brimhall et al. ............... 494/10 |
| 4,755,300 A | 7/1988 | Fischel et al. |
| 4,755,301 A | 7/1988 | Bowers |
| 4,770,779 A | 9/1988 | Ichikawa et al. |
| 4,776,964 A | 10/1988 | Schoendorfer et al. |
| 4,818,291 A | 4/1989 | Iwatsuki et al. |
| 4,818,386 A | 4/1989 | Burns |
| 4,828,710 A | 5/1989 | Itoh et al. |
| 4,832,851 A | 5/1989 | Bowers et al. |
| 4,834,890 A | 5/1989 | Brown et al. |
| 4,839,058 A | 6/1989 | Cawley et al. |
| 4,844,818 A | 7/1989 | Smith |
| 4,846,780 A | 7/1989 | Galloway et al. |
| 4,846,974 A * | 7/1989 | Kelley et al. .............. 210/380.1 |
| 4,871,462 A | 10/1989 | Fischel et al. |
| 4,874,368 A | 10/1989 | Miller et al. |
| 4,877,520 A | 10/1989 | Burns |
| 4,879,031 A | 11/1989 | Panzani et al. |
| 4,900,453 A | 2/1990 | Sedlmayer et al. |
| 4,902,281 A | 2/1990 | Avoy |
| 4,928,603 A | 5/1990 | Rose et al. |
| 4,929,242 A | 5/1990 | Desecki et al. |
| 4,943,273 A | 7/1990 | Pages et al. |
| 4,946,601 A | 8/1990 | Fiehler |
| 4,950,220 A | 8/1990 | Wells et al. |
| 4,957,638 A | 9/1990 | Smith |
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'Donnell, Jr. et al. |
| 5,019,243 A | 5/1991 | McEwen et al. |
| 5,030,215 A | 7/1991 | Morse et al. |
| 5,030,341 A | 7/1991 | McEwen |
| 5,045,048 A | 9/1991 | Kaleskas et al. |
| 5,053,127 A | 10/1991 | Schoendorfer et al. |
| 5,071,570 A | 12/1991 | Shiraki et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson |
| 5,152,905 A | 10/1992 | Pall et al. |
| 5,156,613 A | 10/1992 | Sawyer |
| 5,165,938 A | 11/1992 | Knighton |
| 5,171,456 A | 12/1992 | Hwang et al. |
| 5,173,295 A | 12/1992 | Wehling et al. |
| 5,185,001 A | 2/1993 | Galanakis |
| 5,188,583 A | 2/1993 | Guigan et al. |
| 5,190,057 A | 3/1993 | Sarfarazi |
| 5,190,759 A | 3/1993 | Lindblad et al. |
| 5,204,537 A | 4/1993 | Bennet et al. |
| 5,206,023 A | 4/1993 | Hunziker et al. |
| 5,217,426 A | 6/1993 | Bacehowski et al. |
| 5,217,627 A | 6/1993 | Pall et al. |
| 5,219,328 A | 6/1993 | Morse et al. |
| 5,226,877 A | 7/1993 | Epstein |
| 5,234,608 A | 8/1993 | Duff |
| 5,236,604 A | 8/1993 | Fiehler |
| 5,258,126 A | 11/1993 | Pall et al. |
| 5,260,420 A | 11/1993 | Burnouf-Radosevich et al. |
| 5,269,927 A | 12/1993 | Fiehler |
| 5,271,852 A | 12/1993 | Luoma, II |
| 5,279,825 A | 1/1994 | Wehling et al. |
| 5,281,342 A | 1/1994 | Biesel et al. |
| 5,290,552 A | 3/1994 | Sierra et al. |
| 5,290,918 A | 3/1994 | Bui-Khac et al. |

| | | | | | | |
|---|---|---|---|---|---|---|
| 5,298,171 | A | 3/1994 | Biesel et al. | 6,322,785 B1 | 11/2001 | Landesberg et al. |
| 5,304,372 | A | 4/1994 | Michalski et al. | 6,334,842 B1 | 1/2002 | Hlavinka et al. |
| 5,316,674 | A | 5/1994 | Pall et al. | 6,342,157 B1 | 1/2002 | Hood et al. |
| 5,318,524 | A | 6/1994 | Morse et al. | 6,368,298 B1 | 4/2002 | Beretta et al. |
| 5,318,782 | A | 6/1994 | Weis-Fogh | 6,472,162 B1 | 10/2002 | Coelho et al. |
| 5,321,126 | A | 6/1994 | van Dommelen et al. | 6,516,953 B1 | 2/2003 | DiCesare |
| 5,322,620 | A | 6/1994 | Brown et al. | 6,544,162 B1 * | 4/2003 | Van Wie et al. ............. 494/37 |
| 5,330,974 | A | 7/1994 | Pines et al. | 6,563,953 B2 | 5/2003 | DiCesare et al. |
| 5,344,752 | A | 9/1994 | Murphy | 6,629,919 B2 | 10/2003 | Egozy et al. |
| 5,370,802 | A | 12/1994 | Brown | 6,676,629 B2 | 1/2004 | Andrew et al. |
| 5,376,263 | A | 12/1994 | Fischel | 6,758,978 B1 | 7/2004 | Bedell |
| 5,387,187 | A | 2/1995 | Fell et al. | 6,764,531 B2 | 7/2004 | Hogan |
| 5,393,674 | A | 2/1995 | Levine et al. | 6,777,231 B1 | 8/2004 | Katz et al. |
| 5,395,923 | A | 3/1995 | Bui-Khac et al. | 6,905,612 B2 | 6/2005 | Dorian |
| 5,403,272 | A | 4/1995 | Deniega et al. | 6,979,307 B2 | 12/2005 | Beretta et al. |
| 5,405,607 | A | 4/1995 | Epstein | 7,011,644 B1 | 3/2006 | Andrew et al. |
| 5,411,885 | A | 5/1995 | Marx | 7,077,273 B2 | 7/2006 | Ellsworth |
| 5,417,650 | A | 5/1995 | Gordon | 7,179,391 B2 | 2/2007 | Leach et al. |
| 5,420,250 | A | 5/1995 | Lontz | 2002/0076400 A1 | 6/2002 | Katz et al. |
| 5,443,481 | A | 8/1995 | Lee | 2003/0082152 A1 | 5/2003 | Hedrick et al. |
| 5,454,958 | A | 10/1995 | Fiehler | 2003/0191429 A1 | 10/2003 | Andrew et al. |
| 5,456,693 | A | 10/1995 | Conston et al. | 2004/0171146 A1 | 9/2004 | Katz et al. |
| 5,456,885 | A | 10/1995 | Coleman et al. | 2004/0182788 A1 | 9/2004 | Dorian |
| 5,484,383 | A | 1/1996 | Fitch, Jr. et al. | 2004/0182795 A1 | 9/2004 | Dorian et al. |
| 5,494,578 | A | 2/1996 | Brown et al. | 2005/0076396 A1 | 4/2005 | Katz et al. |
| 5,494,592 | A | 2/1996 | Latham, Jr. et al. | 2005/0084961 A1 | 4/2005 | Hedrick et al. |
| 5,505,685 | A | 4/1996 | Antwiler et al. | 2005/0109716 A1 | 5/2005 | Leach et al. |
| 5,510,102 | A | 4/1996 | Cochrum | 2005/0153441 A1 | 7/2005 | Hedrick et al. |
| 5,533,518 | A | 7/1996 | Vogler | 2005/0153442 A1 | 7/2005 | Katz et al. |
| 5,560,830 | A | 10/1996 | Coleman | 2005/0196874 A1 | 9/2005 | Dorian et al. |
| 5,577,513 | A | 11/1996 | Vlasselaer | 2005/0247715 A1 | 11/2005 | Ellsworth et al. |
| 5,585,007 | A | 12/1996 | Antanavich et al. | 2005/0260174 A1 | 11/2005 | Fraser et al. |
| 5,589,462 | A | 12/1996 | Patat et al. | 2005/0260175 A1 | 11/2005 | Hedrick et al. |
| 5,601,727 | A | 2/1997 | Bormann et al. | 2005/0282275 A1 | 12/2005 | Katz et al. |
| 5,607,579 | A | 3/1997 | Latham, Jr. et al. | 2006/0083720 A1 | 4/2006 | Fraser et al. |
| 5,614,106 | A | 3/1997 | Payrat et al. | 2006/0175242 A1 | 8/2006 | Dorian et al. |
| 5,632,905 | A | 5/1997 | Haynes | 2006/0196885 A1 | 9/2006 | Leach et al. |
| 5,641,622 | A | 6/1997 | Lake et al. | 2006/0243676 A1 | 11/2006 | Swift et al. |
| 5,643,192 | A | 7/1997 | Hirsh et al. | 2007/0036768 A1 | 2/2007 | Fraser et al. |
| 5,674,173 | A | 10/1997 | Hlavinka et al. | 2007/0075016 A1 | 4/2007 | Leach |
| 5,733,545 | A | 3/1998 | Hood et al. | 2008/0011684 A1 | 1/2008 | Dorian et al. |
| 5,736,033 | A | 4/1998 | Coleman et al. | 2008/0283474 A1 | 11/2008 | Leach et al. |
| 5,788,662 | A | 8/1998 | Antanavich et al. | | | |
| 5,795,489 | A | 8/1998 | Holm et al. | FOREIGN PATENT DOCUMENTS | | |
| 5,795,571 | A | 8/1998 | Cederholm-Williams et al. | BR | 9103724 | 3/1993 |
| 5,853,600 | A | 12/1998 | McNeal et al. | CA | 1321138 | 8/1993 |
| 5,860,937 | A | 1/1999 | Cohen | CA | 2182862 | 6/1996 |
| 5,889,584 | A | 3/1999 | Wardlaw | CN | 1074709 | 7/1993 |
| 5,918,622 | A | 7/1999 | Perez | DE | 56103 | 10/1860 |
| 5,924,972 | A | 7/1999 | Turvaville et al. | DE | 1443359 | 11/1968 |
| 5,980,757 | A | 11/1999 | Brown et al. | DE | 4202667 | 5/1993 |
| 6,011,490 | A | 1/2000 | Tonnesen et al. | EP | 090997 | 10/1983 |
| 6,022,306 | A | 2/2000 | Dumont et al. | EP | 0102773 | 3/1984 |
| 6,025,201 | A | 2/2000 | Zelmanovic et al. | EP | 0109374 | 5/1984 |
| 6,051,146 | A | 4/2000 | Green et al. | EP | 0142339 | 5/1985 |
| 6,053,856 | A | 4/2000 | Hlavinka | EP | 0253198 | 1/1988 |
| 6,054,122 | A | 4/2000 | MacPhee et al. | EP | 285891 | 10/1988 |
| 6,063,297 | A | 5/2000 | Antanavich et al. | EP | 0295771 | 12/1988 |
| 6,071,423 | A | 6/2000 | Brown et al. | EP | 0295771 A | 12/1988 |
| 6,090,793 | A | 7/2000 | Zimmermann et al. | EP | 0417818 | 3/1991 |
| 6,096,309 | A | 8/2000 | Prior et al. | EP | 0534178 | 3/1993 |
| 6,102,843 | A | 8/2000 | Kelley et al. | EP | 0592242 | 4/1994 |
| 6,117,425 | A | 9/2000 | MacPhee et al. | EP | 1005910 | 6/2000 |
| 6,153,113 | A | 11/2000 | Goodrich et al. | EP | 1005910 A | 6/2000 |
| 6,196,987 | B1 | 3/2001 | Holmes et al. | EP | 1427279 A1 | 6/2004 |
| 6,197,325 | B1 | 3/2001 | MacPhee et al. | EP | 1467746 A2 | 10/2004 |
| 6,200,287 | B1 | 3/2001 | Keller et al. | EP | 1670315 A2 | 6/2006 |
| 6,214,338 | B1 | 4/2001 | Antanavich et al. | EP | 1716901 A1 | 11/2006 |
| 6,245,900 | B1 | 6/2001 | Yamasaki et al. | GB | 854715 | 11/1960 |
| 6,277,961 | B1 | 8/2001 | Hock et al. | JP | 60-053845 | 3/1985 |
| 6,280,400 | B1 | 8/2001 | Niermann | JP | 2036872 | 2/1990 |
| 6,296,602 | B1 | 10/2001 | Headley | JP | 02071747 | 3/1990 |
| 6,316,247 | B1 | 11/2001 | Katz et al. | | | |

| | | |
|---|---|---|
| JP | 6250014 | 9/1994 |
| JP | 02129224 | 10/2000 |
| MX | 246078 | 5/2007 |
| WO | WO-8400905 | 3/1984 |
| WO | WO-8802259 | 4/1988 |
| WO | WO-9010031 | 9/1990 |
| WO | WO-9222312 | 12/1992 |
| WO | WO-9305067 | 3/1993 |
| WO | WO-9308904 | 5/1993 |
| WO | WO 93/08904 | 9/1993 |
| WO | WO-9407548 | 4/1994 |
| WO | WO-9617871 | 6/1996 |
| WO | WO 98/48938 * 11/1998 | ............... 494/37 |
| WO | WO 01/03756 A | 1/2001 |
| WO | WO-0103756 | 1/2001 |
| WO | WO/01/83068 | 11/2001 |
| WO | WO-0183068 | 11/2001 |
| WO | WO-0224107 | 3/2002 |
| WO | WO 03/015800 | 2/2003 |
| WO | WO-03015800 | 2/2003 |
| WO | WO-03092894 A2 | 11/2003 |
| WO | WO 2004/009207 | 1/2004 |
| WO | WO-2004009207 | 1/2004 |
| WO | WO-2004104553 A2 | 12/2004 |
| WO | WO-2007142908 A1 | 12/2007 |

OTHER PUBLICATIONS

Anesthesiology, vol. 81, No. 4, pp. 1074-1077, Oct. 1994, Hiromasa Mitsuhata, M.D., et al., "An Anaphylactic Reaction to Topical Fibrin Glue".

Ann Thorac Surg, vol. 53, pp. 530-531, 1992, Mehmet C. Oz, M.D., et al., "Autologous Fibrin Glue From Intraoperatively Collected Platelet-Rich Plasma".

Ann Thorac Surg, vol. 56, pp. 387-389, 1993, Robert L. Quigley, M.D., et al., "Intraoperative Procurement of Autologous Fibrin Glue".

Berguer, R., R. L. Staerkel, E. E. Moore, F. A. Moore, W. B. Galloway, and M. B. Mockus. "Warning: fatal reaction to the use of fibrin glue in deep hepatic wounds. Case reports." *J Trauma* 31 (3 1991): 408-11.

Berruyer, M., J. Amiral, P. Ffrench, J. Belleville, O. Bastien, J. Clerc, A. Kassir, S. Estanove, and M. Dechavanne. "Immunization by bovine thrombin used with fibrin glue during cardiovascular operations. Development of thrombin and factor V inhibitors " *J Thorac Cardiovasc Surg* 105 (5 1993): 892-7.

Biopolymers, vol. 27, pp. 763-774, 1988, Gerald Marx, "Mechanism of Fibrin Coagulation Based on Selective, Cation-Driven, Protofibral Association".

Casali, B., F. Rodeghiero, A. Tosetto, B. Palmieri, R. Immovilli, C. Ghedini, and P. Rivasi. "Fibrin glue from single-donation autologous plasmapheresis." Transfusion 32 (7 1992): 641-3.

Collier, B.S. et al., "The pH Dependence of Quantitative Ristocetin-induced Platelet Aggregation: Theoretical and Practical Implications—A New Device for Maintenance of Platelet-Rich Plasma pH", Hematology Service, Clinical Pathology Department, Clinical Center, National Institutes of Health, Bethesda, Md. 20014, Blood, vol. 47, No. 5 May 1976.

DelRossi, A. J., A. C. Cernaianu, R. A.Vertrees, C. J. Wacker, S. J. Fuller, J. Cilley Jr., and W. A. Baldino. "Platelet-rich plasma reduces postoperative blood loss after cardiopulmonary bypass." *J Thorac Cardiovasc Surg* 100 (2 1990): 281-6.

Drug Intelligence and Clinical Pharmacy, vol. 22, pp. 946-952, Dec. 1988, Dennis F. Thompson, et al., "Fibrin Glue: A Review of Its Preparation, Efficacy, and Adverse Effects as a Topical Hemostat".

Edlich, Richard F., George T. Rodeheaver, and John G. Thacker. "Surgical Devices in Wound Healing Management." In *Wound Healing: Biochemical & Clinical Aspects*,ed. I. Kelman Cohen, Robert F. Diegelmann, and William J. Lindblad. 581-600. 1st ed., vol. Philadelphia: W.B. Saunders Company, 1992).

Epstein, G. H., R. A. Weisman, S. Zwillenberg, and A. D. Schreiber. "A new autologous fibrinogen-based adhesive for otologic surgery." *Ann Otol Rhino Laryngol* 95 (1 Pt 11986): 40-5.

First clinical results: Kuderma, H. and Helene Matras. "Die klinische Anwendung der Klebung van Nervenanastomosen mit Gerinnungssubstanzen bei der Rekonstruction verletzter peripherer Nerven." Wein Klin Wochenschr 87 (15 1975): 495-501.

Gibble, J. W. and P. M. Ness. "Fibrin glue: the perfect operative sealant?" *Transfusion* 30 (8 1990): 741-7.

Harris, E.L.V. Concentration of the Extract. In. Protein Purification Methods: A Practical Approach Harris, E.L.V.; Angal, S.; Editors. (1989) Publisher: (IRL Press, Oxford, UK), pp. 67-69.

Hartman, A. R., D. K. Galanakis, M. P. Honig, F. C. Seifert, and C. E. Anagnostopoulos. "Autologous whole plasma fibrin gel. Intraoperative procurement." *Arch Surg* 127 (3 1992): 357-9.

Hennis, H. L., W. C. Stewart, and E. K. Jeter. "Infectious disease risks of fibrin glue [letter]." *Ophthalmic Surg* 23 (9 1992): 640.

Jackson, C. M. And Y. Nemerson. "Blood coagulation." *Annu Rev Biochem* 49 (811 1980): 765-811).

Journal of Biomaterials Applications, vol. 7, pp. 309-353, Apr. 1993, David H. Sierra, "Fibrin Sealant Adhesive Systems: A review of their Chemistry, Material Properties and Clinical Appllications".

Journal of Oral Maxillofacial Surgery, vol. 43, pp. 605-611, 1985, Helene Matras, M.D., "Fibrin Seal: The State of the Art".

Kjaergard, H. K,, U. S. Weis-Fogh, H. Sorensen, J. Thiis, and I. Rygg. "A simple method of preparation of£ autologous fibrin glue by means of ethanol." *Surg Gynecol Obstet* 175 (1 1992): 72-3.

Kjaergard, H. K., Fogh Us Weis, and J. J. Thiis. "Preparation of autologous fibrin glue from pericardial blood." *Ann Thorac* Sur 55 (2 1993): 543-4.

Laryngoscope vol. 99, pp. 974-976, Sep. 1989, Kyosti Laitakari, M.D., et al., "Autologous and Homologous Fibrinogen Sealants: Adhesive Strength".

Laryngoscope, vol. 95, pp. 1074-1076, Sep. 1985, Karl H. Siedentop, M.D., et al., "Autologous Fibrin Tissue Adhesive".

Laryngoscope, vol. 96, pp. 1062-1064, Oct. 1986, Karl H. Siedentop, M.D., et al., "Extended Experimental and Preliminary Surgical Findings with Autologous Fibrin Tissue Adhesive Made from Patient's Own Blood".

Lerner, R. and N. S. Binur. "Current status of surgical adhesives." *J Surg Res* 48 (2 1990): 165-81.

Matras, Helene, H. P. Dinges, H. Lassmann, and B. Mamoli. "Zur nahtlosen interfaszikularen Nerventransplantation im Tierexperiment." Wein Med Woschtr 122 (37 1972): 517-523.

Moretz, W., Jr., J Shea Jr., J. R. Emmett, and J Shea. "A simple autologous fibrinogen glue for otologic surgery." *Otolaryngol Head Neck Surg* 95 (1 1986): 122-4.

Otolaryngologic Clinics of North America, vol. 27, No. 1, pp. 203-209, Feb. 1994, Dean M. Toriumi, M.D., et al., "Surgical Tissue Adhesives in Otolaryngology-Head and Neck Surgery".

Sanal, M. "Does fibrin glue cause foreign body reactions? [letter]." *Eur J Pediatr Surg* 3 (3 1993): 190 (1 page).

Sanal, M., H. Dogruyol, A. Gurpinar, and O. Yerci. "Does fibrin glue cause foreign body reactions?" *Eu r J Pediatr Surg* 2 (5 1992): 285-6.

The American Journal of Surgery, vol. 168, pp. 120-122, Aug. 1994, Roy L. Tawes, Jr., M.D., et al., "Autologous Fibrin Glue: The Last Step in Operative Hemostatis".

The American Surgeon, vol. 55, pp. 166-168, Mar. 1989, William D. Spotnitz, M.D., et al., "Successful Use of Fibrin Glue During 2 Years of Surgery at a University Medical Center".

Vortech™ Concentration System, "Do you want a sticky gel to improve the handling of your bone graft?, Platelet Rich Plasma Concentrate, High Volume in 5 Minutes," Biomet Biologics, Inc., Aug. 2005.

Vox Sanquinis, vol. 68: 82-89, Feb. 1995, Boomgaard et. al, Pooled Platelet Concentration Prepred by the . . . .

Weis-Fogh, U. S. "Fibrinogen prepared from small blood samples for autologous use in a tissue adhesive system." *Eur Surg* Res 20 (5-6 1988): 381-9.

Wiseman, David M., David T. Rovee, and Oscar M. Alverez. "Wound Dressings: Design and Use." In *Wound Healing: Biochemical & Clinical Aspects*, ed. I. Kelman Cohen, Robert F. Diegelmann, and William J. Lindblad. 562-580. 1st ed., vol. Philadelphia: W. B. Saunders Company, 1992).

International Search Report and Written Opinion for PCT/US2006/003599 mailed Aug. 21, 2006.

International Search Report and Written Opinion for PCT/US2006/003597 mailed Feb. 6, 2006.

International Search Report and Written Opinion mailed Aug. 12, 2008 for PCT/US07/17055.

International Preliminary Report on Patentability mailed Feb. 12, 2009, for PCT/US2007/017055 filed Jul. 31, 2007, which claims benefit of U.S. Appl. No. 60/834,550, filed Jul. 31, 2006, based on U.S. Appl. No. 60/723,312, filed Oct. 4, 2005; U.S. Appl. No. 60/654,718, filed Feb. 17, 2005; and U.S. Appl. No. 60/651,050, filed Feb. 7, 2005.

"Cell Isolation Techniques, Methods and Materials, Working with Enzymes," (2004) (9 pages) Worthington Biochemical Corp.

"Cell Isolation Theory, Tissue Types," (2004) (5 pages) Worthington Biochemical Corp.

"Cytori Celution Cell Concentrate Device," Exhibit 14, 510(k) Summary, FDA approval K060482 (Sep. 28, 2006).

"Frequently Asked Questions, 1. Kits, 2. Engzymes," (2003) 3 pages Worthington Biochemical Corp.

"Sefar Solutions for the Healthcare Industry," brochure (2003) 9 pages Sefar Medifab®.

"Trypsinization of Adherent Cells," (undated) 2 pages.

DeUgarte, M.D., Daniel A., et al., "Future of Fat as Raw Material for Tissue Regneration," (2007) pp. 215-219, Lippincott Williams & Wilkins, Inc.

DiMuzio, Paul et al., "Development of a Tissue-Engineered Bypass Graft Seeded with Stem Cells," Vasucular, vol. 14, No. 6, (2006) pp. 338-342, BC Decker, Inc.

Frasier, John K., et al., "Plasticity of human adipose stem cells toward endothelial cells and cardiomyocytes," Nature Clinical Practice Cardiovascular Medicine, vol. 3, Supplement 1 (Mar. 2006) pp. S33-S37.

Gimble, Jeffrey M., "Adipose-Derived Stem Cells for Regenerative Medicine," Circulation Research (2007) pp. 1249-1260, American Heart Association, Inc.

Gomillion, Cheryl T., et al., "Stem cells and adipose tissue engineering," Biomaterials 27, Science Direct (2006) pp. 6052-6063, Elsevier.

GPS® III System, GPS® III Platelet Separation System, Leadership through Technology, brochure, Jul. 2007 (8 sheets).

GPS® System, "GPS® Platelet Concentrate System," Cell Factor Technologies, Inc., Biomet Orthopaedics, Inc., (2004) (9 pages).

GPS® System, "Shoulder Recovery with the GPS® Platelet Concentrate System, Rotator Cuff Surgical Techniques," brochure, Cell Factor Technologies, Inc., Biomet Orthopaedics, Inc., (2004) 6 pages.

GPS® System, "Shoulder Recovery with the GPS® Platelet Concentrate System, Rotator Cuff Surgical Techniques," Cell Factor Technologies, Inc., Biomet Orthopaedics, Inc., (2004) 3 pages, http://www.cellfactortech.com/global_products.cfm, printed Sep. 16, 2005.

GPS®II System, Gravitational Platelet Separation System, "Accelerating the Body's Natural Healing Process," Cell Factor Technologies, Inc., Biomet Europe (2005) 16 pages, http://www.cellfactortech.com/global_products.cfm, printed Sep. 16, 2005.

GPS®II System, Gravitational Platelet Separation System, "User Manual," Cell Factor Technologies, Inc., Biomet Europe [date unknown] 13 pages, http://www.cellfactortech.com/global_products.cfm, printed Sep. 16, 2005.

Guilak, Frank, et al., "Adipose-derived adult stem cells for cartilage tissue engineering," Biorheology 41 (2004) pp. 389-399, IOS Press.

Hattori, et al., "Osteogenic Potential of Human Adipose Tissue-Derived Stromal Cells as an Alternative Stem Cell Source," Cells Tissues Organs (2004) 178:2-12 Karger.

International Search Report and Written Opinion mailed Jul. 3, 2009 for PCT/US2009/035564 claiming benefit of U.S. Appl. No. 61/078,178, filed Jul. 3, 2008.

Lendeckel, Stefan, et al., "Autologous stem cells (adipose) and fibrin glue used to treat widespread traumatic calvarial defects: case report," Journal of Cranio-Maxillofacial Surgery (2004) European Association for Cranio-Maxillofacial Surgery.

Marrowstim™ Concentration System, (2008) 20 pages Biomet Biologics, Inc.

Nakagami, Hironori, et al., "Novel Autologous Cell Tehrapy in Ischemic Limb Disease Through Growth Factor Secretion by Cultured Adipose Tissue-Derived Stromal Cells," Angiogenesis by Adipose Tissue-Derived Cells, (2005) pp. 2542-2547, American Heart Association, Inc.

Nathan, Suresh,, et al., "Cell-Based Therapy in the Repair of Osteochondral Defects: A Novel Use for Adipose Tissue," Tissue Engineering, vol. 9, No. 4 (2003) pp. 733-744 Mary Ann Liebert, Inc.

Parker, Anna M., et al., Adipose-derived stem cells for the regeneration of damaged tissues, Expert Opinion, Cell- & Tissue-based Therapy, Expert Opin. Biol. Ther. (2006) pp. 567-578 Informa UK Ltd.

Planat-Bénard, V., et al., "Spontaneous Cardiomyocyte Differentiation From Adipose Tissue Stroma Cells," Adipose-Derived Cell Cardiomyocyte (2004) pp. 223-229 American Heart Association, Inc.

Plasmax™ Plasma Concentrate, brochure (2006) 5 pages Biomet Biologics, Inc.

Rangappa, Sunil, M.D., "Transformation of Adult Mesenchymal Stem Cells Isolated From the Fatty Tissue Into Cardiomyocytes," Adult Stem Cells Transformed into Cardiomyoctyes, (2003) pp. 775-779 Ann Thorac Surg.

Rigotti, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Breast, PRS Journal vol. 119, No. 5, Stem Cell Therapy for Angiogenesis, (Pub. 2005) pp. 1409-1422.

Rubin, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Discussion vol. 119, No. 5, Stem Cell Therapy for Angiogenesis, (2007) pp. 1423-1424.

Schäffler, Andreas, et al., "Concise Review: Adipose Tissue-Derived Stromal Cells—Basic and Clinical Implications for Novel Cell-Based Therapies," Tissue-Specific Stem Cells, Stem Cells® (2007) pp. 818-827 AlphaMed Press.

Sigma-Aldrich® Alkaline Phosphatase (Procedure No. 85), drug fact sheet, (2003) pp. 1-2, Sigma-Aldrich, Inc.

Takahashi, Kazutoshi et al., "Induction of Pluripotent Stem Cells from Adult Human Fibroblasts by Defined Factors," Cell, (2007) pp. 1-12, Elsevier Inc.

Yoon, Eulsik, M.D., Ph.D., et al., "In Vivo Osteogenic Potential of Human Adipose-Derived Stem Cells/Poly Lactide-Co-Glycolic Acid Constructs for Bone Regneration in a Rat Critical-Sized Calvarial Defect Model," Tissue Engineering, vol. 13, No. 3 (2007) pp. 619-627 Mary Ann Liebert, Inc.

Zhang, Duan-zhen, et al., "Transplantation of autologous adipose-derived stem cells ameliorates cardiac function in rabbits with myocardial infarction," Chinese Medical Journal, vol. 120, No. 4 (2007) pp. 300-307 General Hospital of Shenyang Military Region, Shenyang, China.

Zuk, Patricia A., Ph.D., "Multilineage Cells from Human Adipose Tissue: Implications for Cell-Based Therapies," Tissue Engineering, vol. 7, No. 2, (2001) pp. 211-228 Mary Ann Liebert, Inc.

* cited by examiner

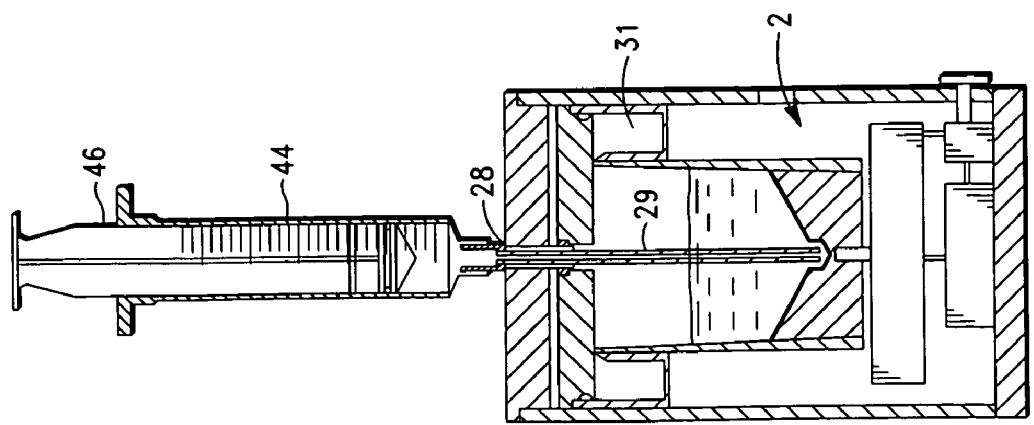
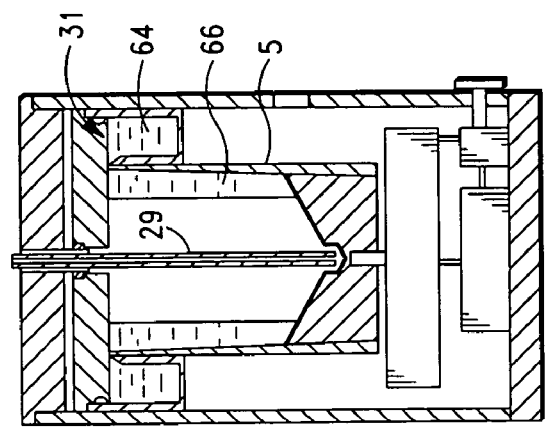
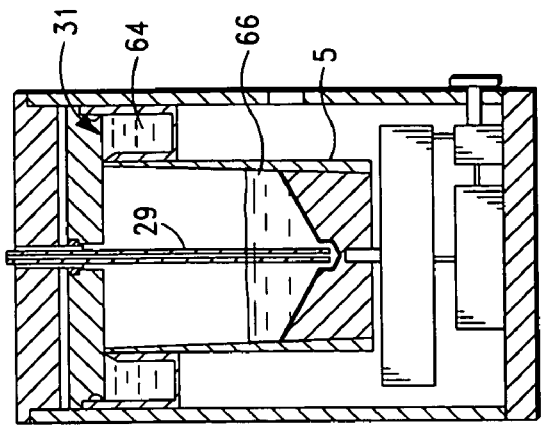

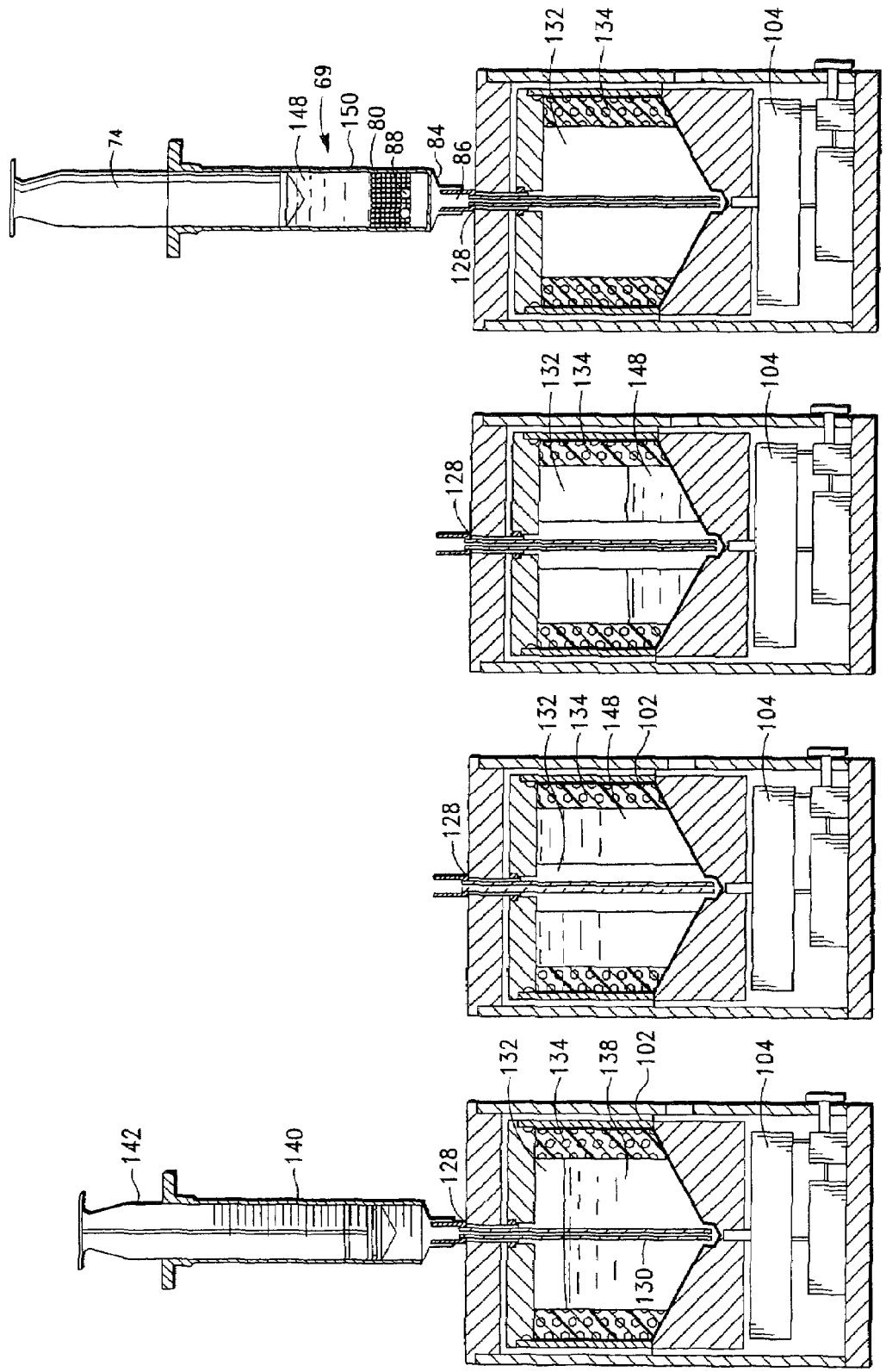

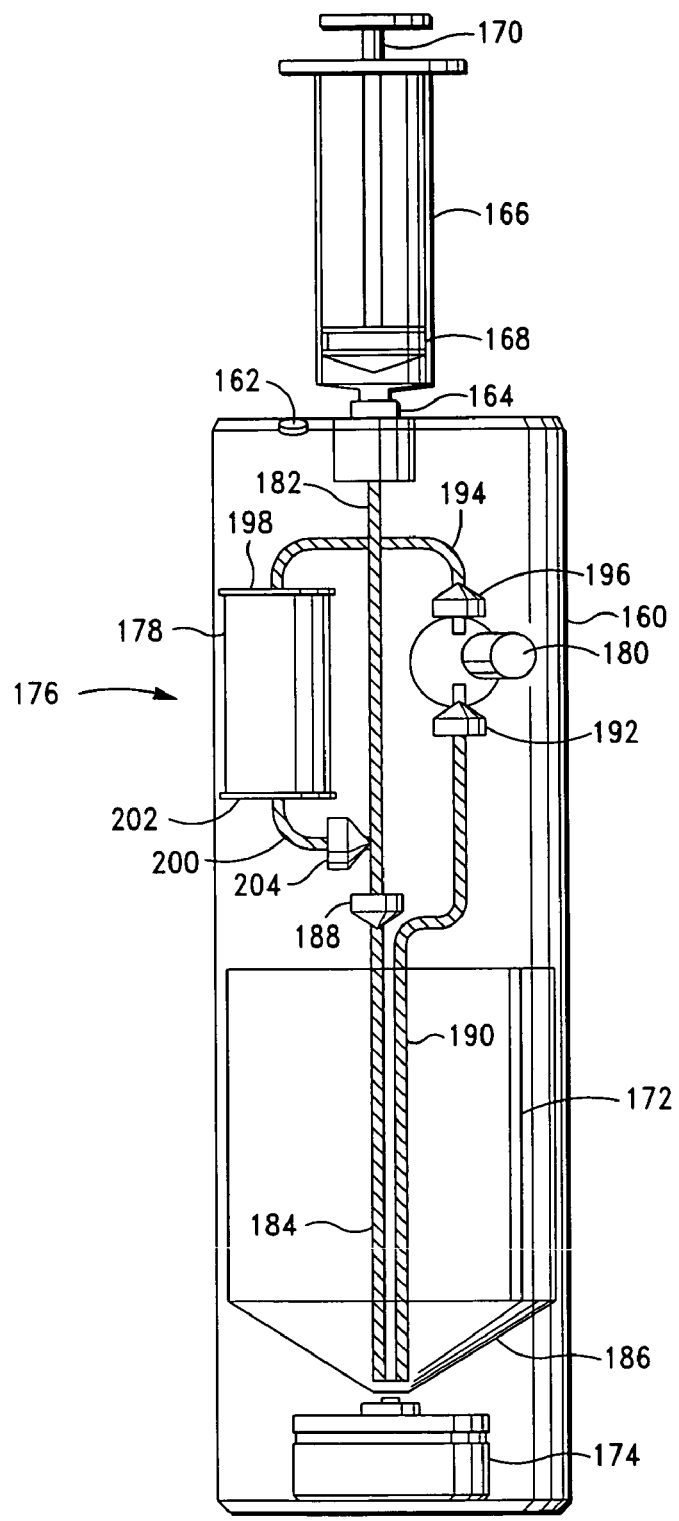
FIG.—14

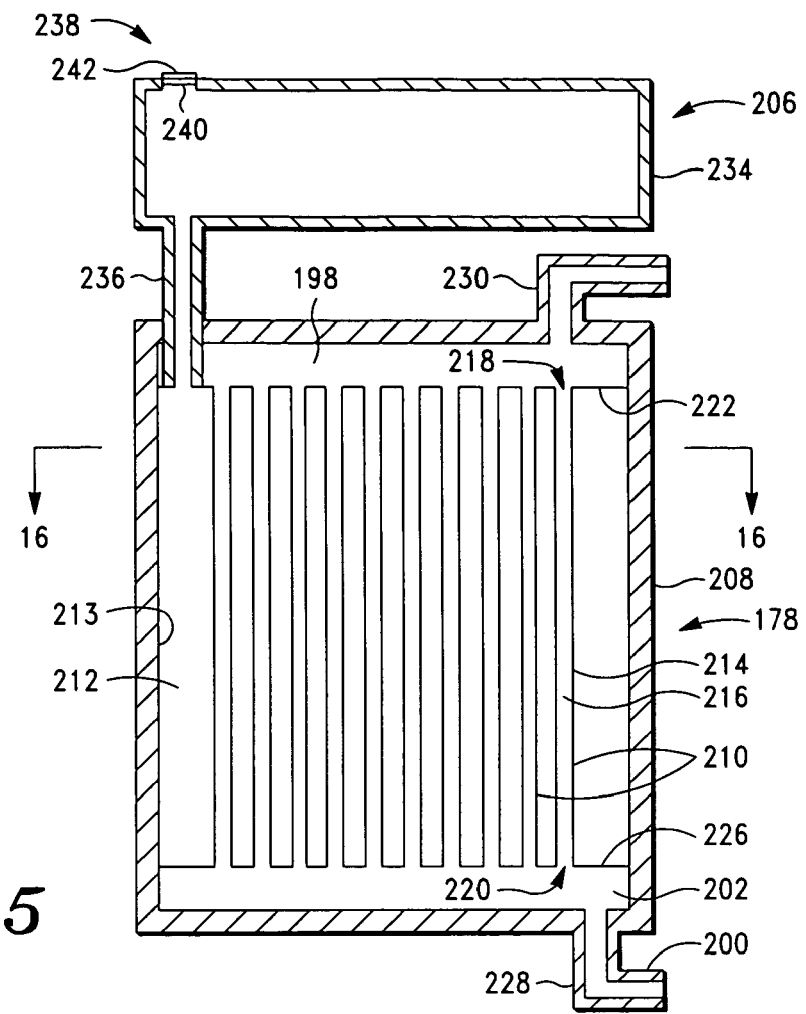
FIG.-15
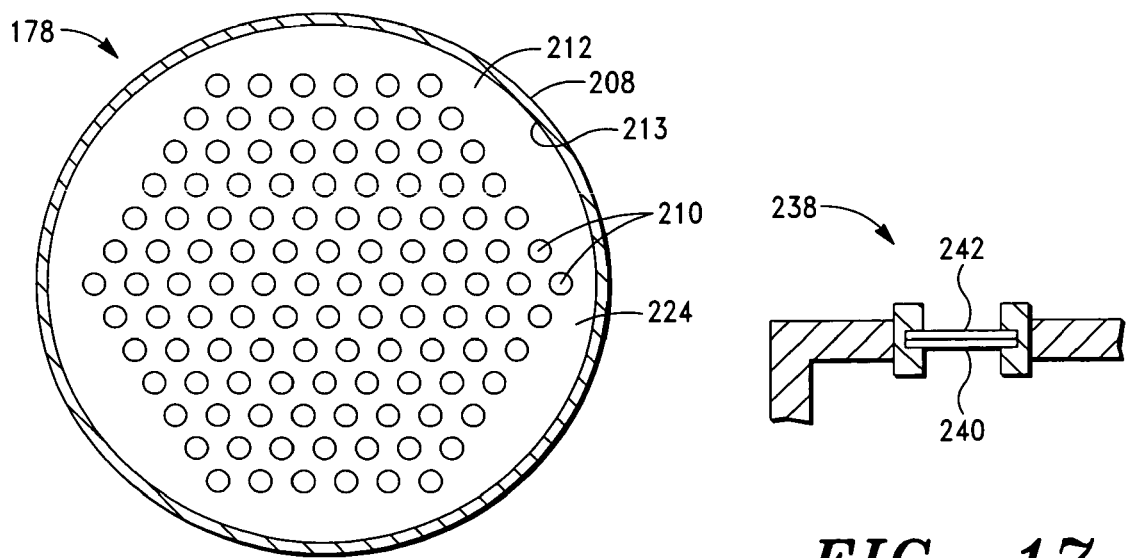
FIG.-16
FIG.-17

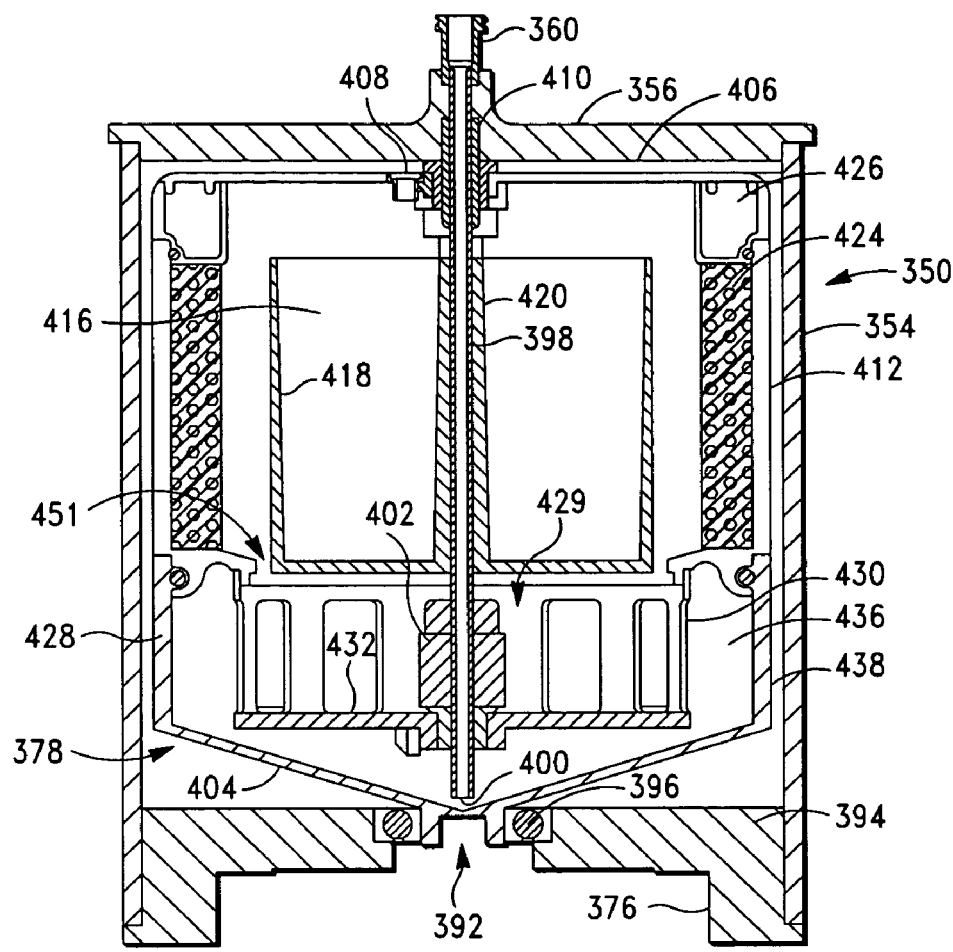
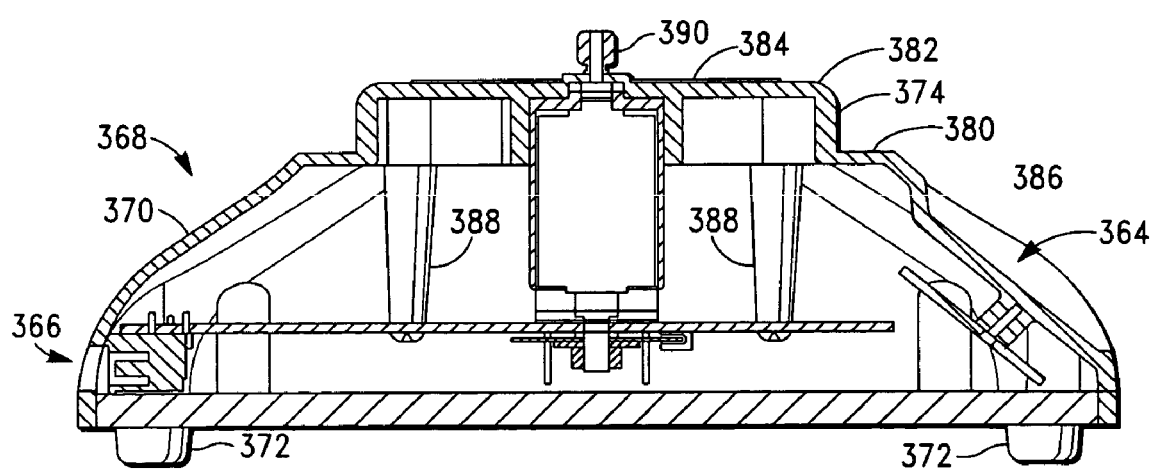
FIG.-21

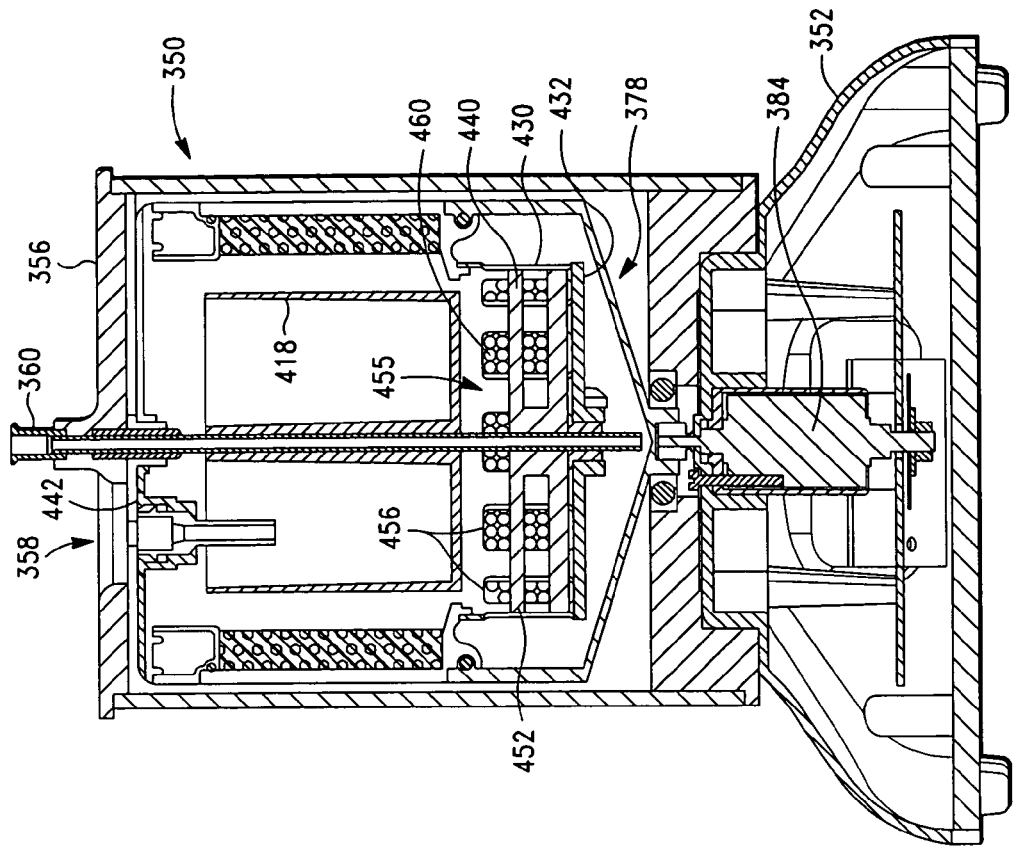
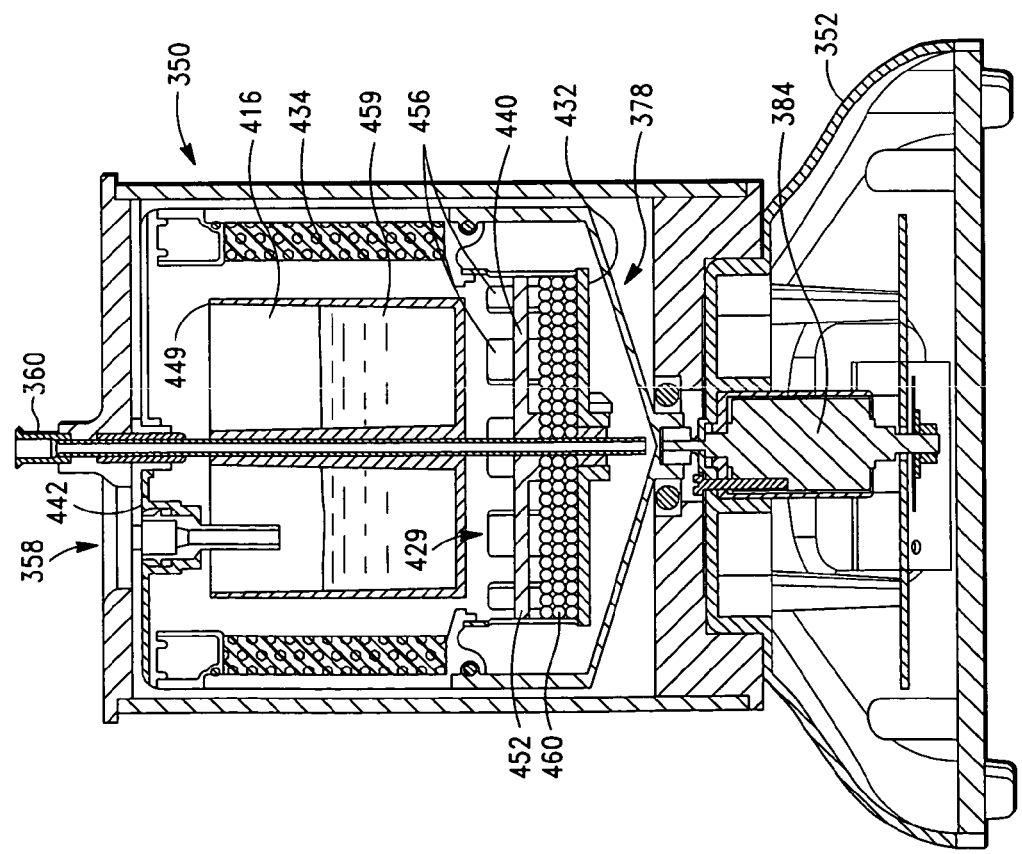

METHOD AND APPARATUS FOR PREPARING PLATELET RICH PLASMA AND CONCENTRATES THEREOF

BENEFIT OF EARLIER FILING DATES UNDER 35 USC 120

This application claims the benefit under 35 USC 120 of the filing dates of Provisional Application No. 60/651,050 filed Feb. 7, 2005, Provisional Application No. 60/654,718 filed Feb. 17, 2005 and Provisional Application No. 60/723,312 filed Oct. 4, 2005.

FIELD OF THE INVENTION

This invention relates to a device and method for preparing platelet-plasma concentrates with improved wound healing properties for use as a tissue sealant and adhesive. The product has a fully active (un-denatured) fibrinogen concentration that is several times greater than is found in blood and a platelet concentration that is many times greater than is found in blood.

BACKGROUND OF THE INVENTION

Blood can be fractionated, and the different fractions of the blood can be used for different medical needs. Under the influence of gravity or centrifugal force, blood spontaneously sediments into three layers. At equilibrium, the top low-density layer is a straw-colored clear fluid called plasma. Plasma is a water solution of salts, metabolites, peptides, and many proteins ranging from small (insulin) to very large (complement components).

The bottom, high-density layer is a deep red viscous fluid comprising anuclear red blood cells (erythrocytes) specialized for oxygen transport. The red color is imparted by a high concentration of chelated iron or heme that is responsible for the erythrocytes' high specific gravity. The relative volume of whole blood that consists of erythrocytes is called the hematocrit, and in normal human beings this can range from about 37% to about 52% of whole blood.

The intermediate layer is the smallest, appearing as a thin white band above the erythrocyte layer and below the plasma layer; this is called the buffy coat. The buffy coat itself has two major components, nucleated leukocytes (white blood cells) and anuclear smaller bodies called platelets (or thrombocytes). Leukocytes confer immunity and contribute to debris scavenging. Platelets seal ruptures in blood vessels to stop bleeding, and deliver growth and wound healing factors to a wound site. Slower speed or shorter duration centrifugation permits separation of erythrocytes and leucocytes from plasma, while the smaller platelets remain suspended in the plasma, resulting in PRP.

A major improvement in making plasma concentrate from whole blood for use in wound healing and as a tissue sealant is described in U.S. Pat. No. 5,585,007; this patent is hereby incorporated by reference in its entirety. This device, designed for placement in a medical laboratory or surgical amphitheatre, used a disposable cartridge for preparing tissue sealant. The device was particularly applicable for stat preparations of autologous tissue sealants. Preparation in the operating room of 5 ml of sealant from 50 ml of patient blood required less than 15 minutes and only one simple operator step. There was no risk of tracking error because processing can be done in the operating room. Chemicals added could be limited to anticoagulant (e.g., citrate) and calcium chloride. The disposable cartridge could fit in the palm of the hand and was hermetically sealed to eliminate possible exposure to patient blood and ensure sterility. Adhesive and tensile strengths of the product were comparable or superior to pooled blood fibrin sealants made with precipitation methods. Use of antifibrinolytic agents (such as aprotinin) was not necessary because the tissue sealant contained high concentrations of natural inhibitors of fibrinolysis from the patient's blood. This new tissue sealant also optionally contained patient platelets and additional factors that promote wound healing, healing factors that are not present in commercially available fibrin sealants.

This device used a new sterile disposable cartridge with the separation chambers for each run. Since the device was designed to be used in a normal medical setting with ample power, the permanent components, designed for long-term durability, safety and reliability, were relatively heavy, using conventional centrifuge motors and accessories.

Small, self-contained centrifugal devices for obtaining platelet concentrates from blood are described in commonly assigned, copending application Ser. No. 10/394,828 filed Mar. 21, 2003, the entire contents of which are hereby incorporated by reference. This device separates blood into erythrocyte, plasma and platelet layers and selectively removes the platelet layer as a platelet concentrate, that is, platelets suspended in plasma. The plasma fraction, being in an unconcentrated form, is not effective as a hemostat or tissue adhesive.

SUMMARY OF THE INVENTION

It is an objective of this invention to provide a compact, self-contained system for producing a concentrate of platelets suspended in concentrated fully active plasma, that is substantially unactivated platelets suspended in plasma concentrated by removing water, leaving the fibrinogen in a fully active form.

The PRP separator-concentrator of the present invention is suitable for office use or emergency use for trauma victims.

One embodiment is a disposable self-contained PRP separator and concentrator unit designed for use with a permanent motor assembly.

Another embodiment is a self-contained disposable PRP separator and concentrator that includes an internal motor and power supply assembly.

A still further embodiment comprises a motorized centrifugal separation unit for preparing PRP.

The PRP separator comprises a motorized centrifugal separation assembly for and an optional concentrator assembly for concentrating the PRP. The centrifugal separator assembly comprises a centrifugal drum separator that includes an erythrocyte capture module and a motor with a drive axis connected to the centrifugal drum separator. The concentrator assembly comprises a water-removal system for preparing PRP concentrate.

The centrifugal drum can have an inner wall surface with an upper edge and a lower edge, a drum bottom, and a central axis; the drum bottom can have a central depression and a floor sloping downward from the lower edge to the center of the central depression.

In the portable, self-contained embodiment of the PRP separator-concentrator of this invention, the motorized centrifugal separation assembly includes a motor having a drive axis, the drive axis being coaxial with the central axis. The motor can have the capacity to rotate the centrifugal drum at a speed of at least 2,000 rpm for 120 seconds. The battery can be connected to the motor through an on/off switch or timer switch, the battery having the capacity to provide sufficient power to complete the separation process. The portable centrifugal separator can be fully enclosed within an outer container, the outer container having a top with a sterile syringe port aligned with the central depression, and an access tube connected to and extending downward from the syringe port.

In one embodiment, the erythrocyte capture module is a depth filter lining the inner wall surface of the centrifugal separator unit, the depth filter having pores sized to capture erythrocytes moving into the pores during centrifugal separation of the erythrocytes from blood and to retain the erythrocytes in the depth filter when centrifugal separation is completed. The term "depth filter", as used herein, is defined as a filter medium that retains contaminants primarily within tortuous passages. It can include an open-cell foam or other matrix made of a material such as a felt that does not significantly activate platelets contacting the surface thereof, whereby erythrocytes moving outward through the plasma during centrifugation move into and are captured by the depth filter leaving behind PRP substantially free from erythrocytes.

In an alternative embodiment of the invention, the inner wall surface of the centrifugal drum can be sloped outwardly from the bottom at an angle of from 1° to 15° with respect to the central axis. The upper edge of the centrifugal drum can be surrounded by an outer, annular erythrocyte capture chamber, the erythrocyte capture chamber including, an outer wall and an inner wall, the outer wall having an upper edge with an elevation higher than the inner wall. The volume of the erythrocyte capture chamber below the top of the inner wall is sized to retain the total volume of separated erythrocytes in the blood while retaining a minimal volume of the PRP. In this embodiment, erythrocytes moving outward through the plasma during centrifugation are retained against the outer wall of the erythrocyte capture chamber and slide downward to substantially fill the lower volume of the erythrocyte capture chamber when centrifugation is ended. During centrifugation, platelets suspended in the liquid in the erythrocyte capture chamber are carried with the flow of plasma displaced by sedimenting erythrocytes so that they travel to the top and over the inner surface of the erythrocyte capture chamber and into the centrifugal drum. Optionally, at least the upper surface of the inner wall of the erythrocyte capture chamber has a slope forming an angle "a" of at least 25° with respect to the central axis for facilitating flow of platelets against the centrifugal force up and over the upper edge of the erythrocyte capture chamber during centrifugation. As the plasma flows from the erythrocyte capture chamber to the centrifugal chamber, the portal or cross-sectional area through which the plasma flows is reduced by the rising slope of the inner wall surface, causing an increase in the plasma flow velocity over the surface and increasing the portion of platelets successfully transported by the plasma.

In one embodiment, the concentrator assembly of the PRP separator-concentrator includes a water-removing hollow fiber cartridge, a pump, and tubing connecting with the hollow fiber cartridge and the pump that circulates PRP in the centrifugal drum through the pump and hollow fiber cartridge and then returns it to the centrifugal drum. In the hollow fiber cartridge, the fibers are ultrafiltration membranes with pores that allow the flow of water through the fiber membrane while excluding the passage of growth factors helpful for healing. The pore structure and surfaces are selected to avoid activation of platelets and disruption of any erythrocytes remaining in the PRP.

In another embodiment, the concentrator assembly includes a plasma concentrating syringe, the syringe having a Luer coupling for connection to the access tube to the center or central depression of the centrifugal drum. In this embodiment, the plasma concentrating syringe comprises a cylindrical barrel with an inner surface and an inlet/outlet port, and a cylindrical actuated piston having an outer surface engaging the inner surface of the barrel. Concentrating beads which can be desiccated hydrogel are positioned between the piston and the inlet/outlet port. A filter is positioned adjacent the inlet/outlet port to prevent escape of the concentrating beads through the inlet/out port. In the operation of the syringe concentrator, movement of the piston in a direction away from the inlet/outlet port draws PRP into the concentrating chamber. Water is removed from the PRP by the concentrating beads, thereby concentrating the PRP without activating the platelets or denaturing the fibrinogen in the plasma. Movement of the piston toward the inlet/outlet port expels concentrated PRP through the inlet/outlet port.

Because the devices of this invention can be operated with standard batteries as their power source, they consume far less power than prior art centrifuge devices, leading to substantial power saving.

A further PRP separator and concentrator embodiment of this invention has a central axis comprises a stationary housing and a rotary assembly mounted for rotation about the central axis with respect to the stationary housing. The rotatable assembly comprises a rotatable centrifugal separator and concentrator and a drive motor. A coupling connects the drive motor and the rotatable assembly, the motor and drive coupling being positioned to rotate the rotatable assembly about the central axis.

The centrifugal separator has an inner separation chamber and an outer erythrocyte capture system. The concentrator comprises a concentration chamber containing desiccated beads. The concentration chamber comprises a floor and a plurality of upright screen supports, the upright screen supports having an inner surface and an outer surface. A cylindrical screen is supported on the outer surface of the upright screen supports.

An axially concentric stationary tube is secured to the housing and extends through the concentration chamber. A stationary bead rake is secured to the tube and extends radially outward. The rake has a distal edge that is positioned adjacent the inner surface of the upright screen supports, With this assemblage, slow rotation of the rotary assembly with respect to the stationary housing pulls the beads past the stationary rake, reducing gel polarization and clumping of the beads.

Each pair of adjacent upright screen supports can define a desiccating bead receptor for holding desiccated beads radially outward from the distal edge of the rake, whereby bead disruption by the rake during high speed rotational phases is substantially avoided.

The separator and concentrator can include a motor controller, wherein the drive motor has a high rotational speed required for centrifugal separation and PRP collection phases and a slow rotational speed required for water removal by desiccated beads, the motor controller include a switch for initiating high and low rotational speeds of the rotary assembly.

The switch initiates high rotational speed of the rotary assembly during centrifugal and PRP concentrate collection phases and initiates low slow rotational speed of the rotary assembly during the PRP concentrate collection phase.

Another rotatable PRP concentrator of this invention has a stationary housing with a central axis, the concentrator including a drive motor and a coupling connecting the drive motor and the centrifugal separator for rotation about its central axis. The concentrator comprises a concentration chamber containing desiccated beads, the concentration chamber comprising a floor and a plurality of upright screen supports. The upright screen supports have an inner surface and an outer surface. A cylindrical screen is supported on the outer surface of the upright screen supports. An axially concentric stationary tube secured to the housing extends through the concentration chamber. A stationary bead rake is secured to the tube and extends radially outward to adjacent the inner surface of the upright screen supports.

With this configuration, slow rotation of the rotary assembly with respect to the stationary housing pulls the beads past the stationary rake, reducing gel polarization and clumping of the beads.

Each pair of adjacent upright screen supports and the screen segments extending therebetween defines a desiccating bead receptor for holding desiccated beads radially outward from the distal edge of the rake, whereby bead disruption by the rake during high speed rotational phases is substantially avoided.

The separator and concentrator can include a motor controller, wherein the drive motor has a high rotational speed required for the PRP collection phase and a slow rotational speed required for water removal by desiccated beads. The motor controller includes a switch for initiating high and low rotational speeds of the rotary assembly. The switch initiates high rotational speed of the rotary assembly during the PRP concentrate collection phase and initiates low slow rotational speed of the rotary assembly during the PRP concentrate collection phase.

BRIEF DESCRIPTION OF DRAWINGS

A more complete appreciation of the invention and many of the attendant advantages thereof will be readily obtained as the same becomes better understood by reference to the following detailed description when considered with the accompanying drawings, wherein:

FIG. 3 is a schematic cross-sectional drawing of the separation separator of FIG. 1 after being loaded with blood.

FIG. 4 is a schematic cross-sectional drawing of the separation separator of FIG. 1 during the spin separation phase.

FIG. 5 is a schematic cross-sectional drawing of the separation separator of FIG. 1 after centrifugation has ended.

FIG. 10 is a schematic cross-sectional drawing of the separation separator of FIG. 9 after being loaded with blood.

FIG. 11 is a schematic cross-sectional drawing of the separation separator of FIG. 10 during the spin separation phase.

FIG. 12 is a schematic cross-sectional drawing of the separation separator of FIG. 10 after centrifugation has ended.

FIG. 13 is a schematic cross-sectional drawing of the separation separator of FIG. 9 after PRP has been drawn into a concentrator syringe.

FIG. 14 is a schematic representation of a combination centrifugal separator and hollow fiber concentrator of this invention.

FIG. 15 is a schematic cross-sectional view of a hollow fiber concentrator according to this invention.

FIG. 16 is a cross-sectional view of the hollow fiber concentrator of FIG. 15, taken along the line 16-16.

FIG. 17 is a schematic cross-sectional view of the membrane valve in the hollow fiber concentrator of FIG. 15.

FIG. 21 is a cross-sectional view of the plasma separator and concentrator of FIG. 20, taken along the line 21-21, exploded along the vertical axis to show the motor drive and drive receptor relationship prior to placing the disposable separator-concentrator assembly on the drive base.

FIG. 24 is a cross-sectional drawing of the device of FIGS. 19-23 after blood has been added.

FIG. 25 is a cross-sectional drawing of the device of FIGS. 19-23 during the centrifugal separation stage producing PRP.

DETAILED DESCRIPTION OF THE INVENTION

This device and method separates plasma-rich plasma from blood and removes water from the plasma-rich plasma without denaturing the fibrinogen or activating the platelets invention. One aspect of the invention is a portable, completely self-contained device that performs this method with a patient's blood to provide an autologous product that is useful as wound healing tissue sealant and adhesive that promotes and speeds healing. Another aspect of the invention is a portable disposable system that can be used with a permanent motorized unit to provide this method and product. A still further aspect is a portable disposable system for producing PRP from a patient's blood.

The devices of this invention are small, portable, self-contained, disposable PRP separation systems. The centrifugal separation modules described with respect to FIGS. 1-13 are one aspect of this invention. They are directed to disposable PRP separation systems that can be used by a medical assistant or doctor without extensive training to prepare PRP and a PRP concentrate from a patient's blood within minutes, with a high recovery of platelets and without significant activation of the platelets. The devices are completely automated and require no user intervention between, first, loading and actuating the device and, second, retrieving the PRP. The devices are able to process bloods of different hematocrits and different plasma densities.

Another more highly automated separator-concentrator of this invention is the combination centrifugal separator and hollow fiber cartridge concentrator shown in FIG. 14. This system requires no user intervention between loading the blood and retrieving PRP concentrate.

Figure 1:
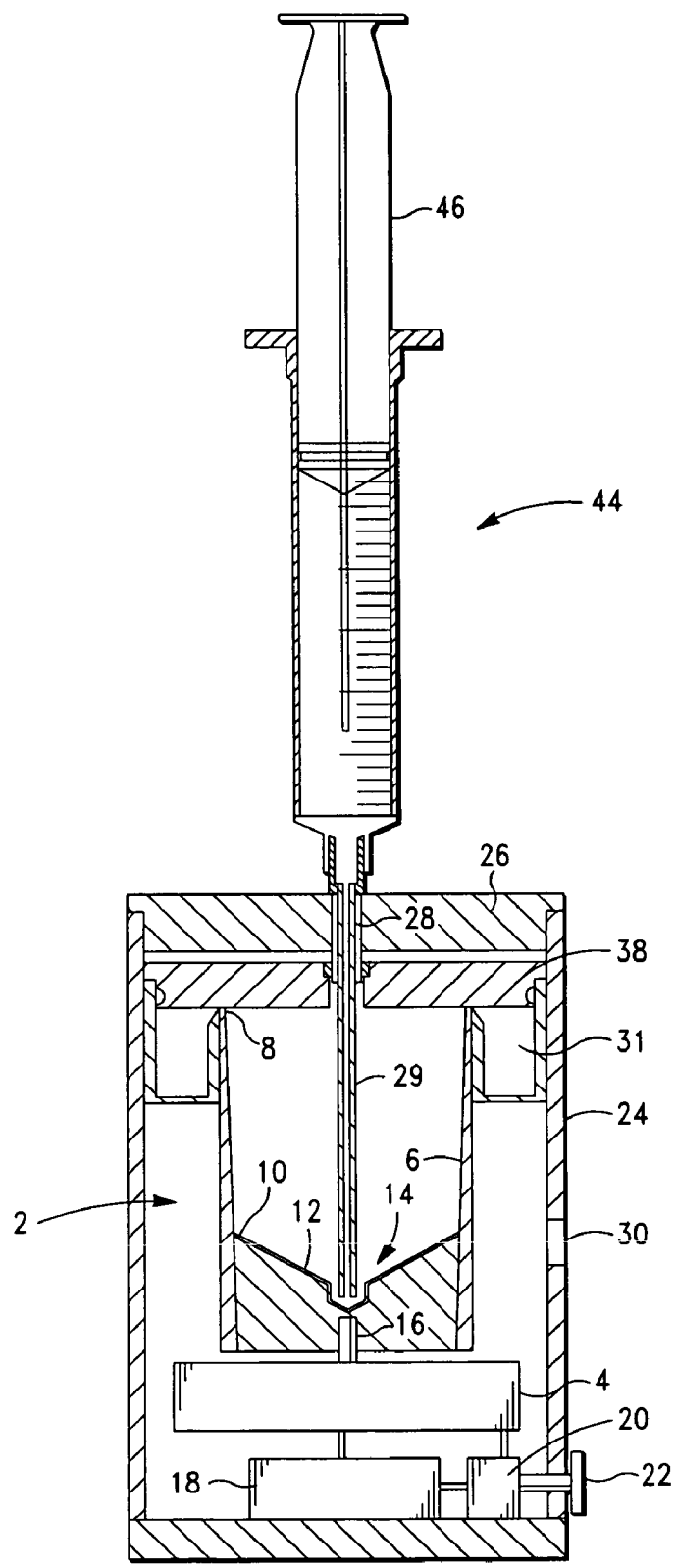
FIG. 1 is a schematic cross-sectional drawing of a centrifugal separator of this invention with an annular erythrocyte trap.
Figure 2:
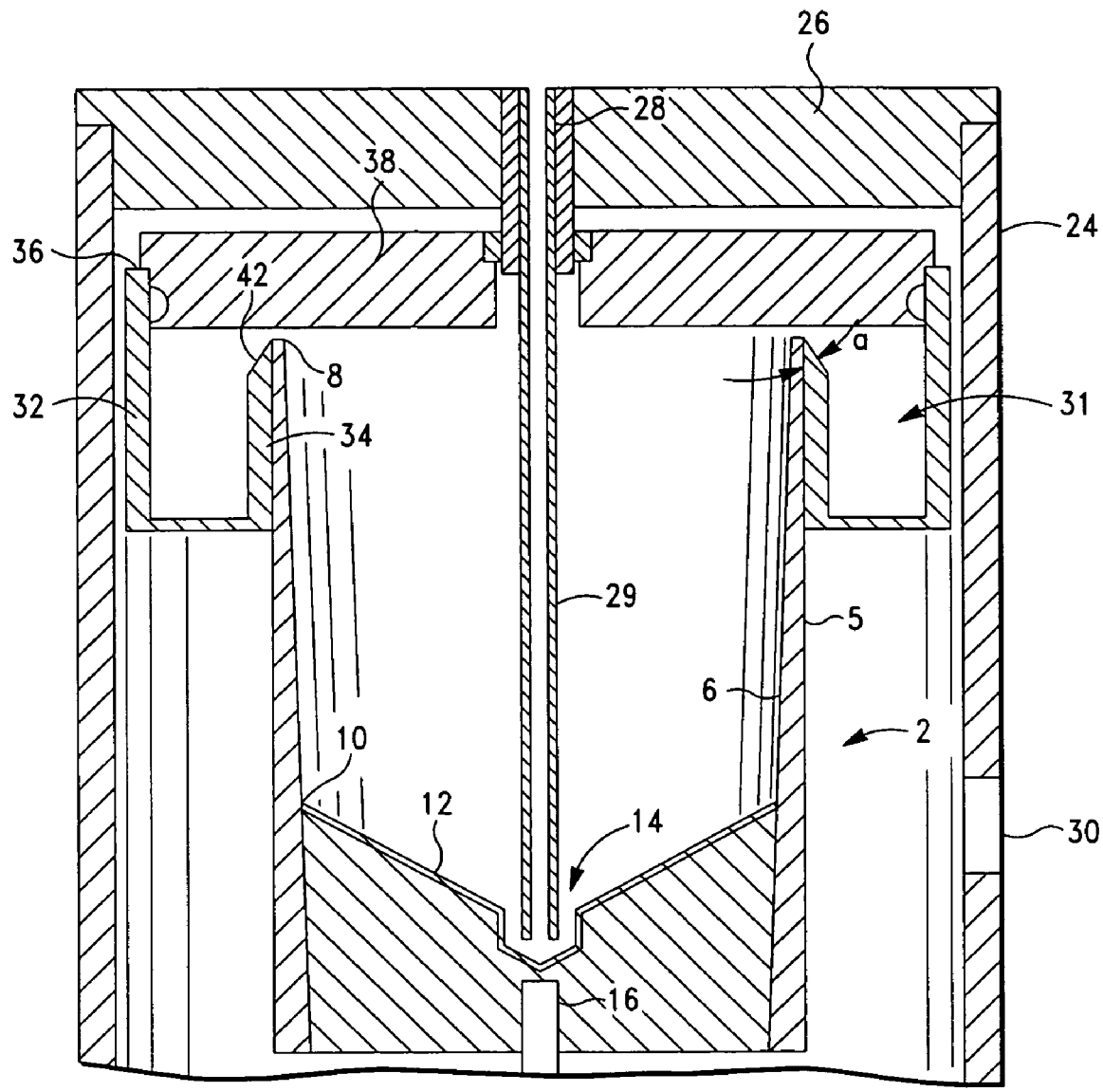
FIG. 2 is a fragmentary cross-sectional drawing of the centrifugal separator and annular erythrocyte trap portion of the centrifugal separator shown in FIG. 1.

FIG. 1 is a schematic cross-sectional drawing of a centrifugal separator of this invention with an annular erythrocyte trap, and FIG. 2 is a fragmentary cross-sectional drawing of the centrifugal separator and annular erythrocyte trap shown in FIG. 1. Referring to FIGS. 1 and 2, the separation system comprises a centrifugal separator unit or chamber 2 and a motor 4. The centrifugal separator unit comprises a centrifugal drum 5 having an inner wall surface 6 with an upper edge 8 and a lower edge 10, a drum bottom 12, and a central axis (not shown). The drum bottom 12 has a central depression 14, the bottom 12 constituting a floor sloping downward from the lower edge 10 to the central depression 14. The motor 4 has a drive axis 16 that is coaxial with the central axis. The motor 4 has the capacity to rotate the centrifugal drum at a speed of at least 2,000 rpm for 120 seconds.

The complete, self-contained unit includes a battery 18 connected to the motor 4 through conventional power connections, the battery 18 having sufficient capacity to complete the separation process. The battery 18 is connected to the motor through an on/off time switch 20 with a manual knob 22.

An outer container 24 encloses the centrifugal separation unit. The container 24 has a top 26 with a sterile syringe port 28 that can be a Luer fitting aligned with the central depression 14. An access tube 29 connects to and extends downward from the syringe port 28 into the separation chamber 2. Tube 29 is used for introducing blood into the separation chamber 2 and for removing PRP from the separation chamber 2 as is explained in greater detail with respect to FIGS. 2-6 hereinafter.

The inner wall surface 6 of the centrifugal drum 5 is sloped outwardly from the bottom 12 at an angle of from 75 to 89° from the central axis. The upper edge 8 of the centrifugal drum 5 is surrounded by an outer, annular erythrocyte capture chamber 31.

Preferably, the outer container 24 for the system is sealed to maintain sterility. To prevent pressure fluctuations from movement of liquid into and from the system, a vent system 30 is provided in a wall of the outer container that permits movement of air out of the container when liquid is introduced and movement of air into the container when liquid is removed. Details of suitable venting systems are described hereinafter with respect to FIGS. 2B and 2C.

Referring to FIG. 2, the erythrocyte capture chamber 31 includes an outer wall 32, and an inner wall 34, the outer wall 32 having a top edge 36 with an elevation higher than the top 8 of the inner wall 6. The vertical distance between the top edge and the top of the inner wall is small, preferably less than 1 mm, but large enough to allow passage of cells, preferably greater than 50 microns. The narrow gap between the top of the inner wall and the top of the chamber serves to minimize the sweeping of erythrocytes from the erythrocyte capture chamber into the centrifugal drum by the swirling wave of PRP during deceleration after completion of the centrifugation step. To further minimize sweeping of erythrocytes back into the centrifuge drum during deceleration, the gap above the inner wall can be filled with a depth filter or screen. The volume of the erythrocyte capture chamber 31 is sized to retain the total volume of separated erythrocytes and leukocytes in the blood while retaining a minimal volume of PRP. An annular cap 38 is secured to the top of the centrifugal drum 5 and the erythrocyte capture chamber 31 in a sealing engagement that prevents escape of blood and blood products from the centrifugal chamber during the centrifugal separation step.

The upper surface portion 42 of the inner wall 34 of the erythrocyte capture chamber 31 can optionally have a slope forming an angle "a" at least 25° with the central axis, facilitating flow of platelets in the PRP flowing inwardly over the upper edge 8 of the erythrocyte capture chamber 31 when the erythrocytes sediment to fill the erythrocyte capture chamber 31.

FIG. 1 shows the separation system coupled with a syringe 44 positioned to introduce blood into the separation chamber 2. The syringe 44 is shown with the plunger or piston 46 in the extended, full position prior to the blood introduction.

Figure 2A:
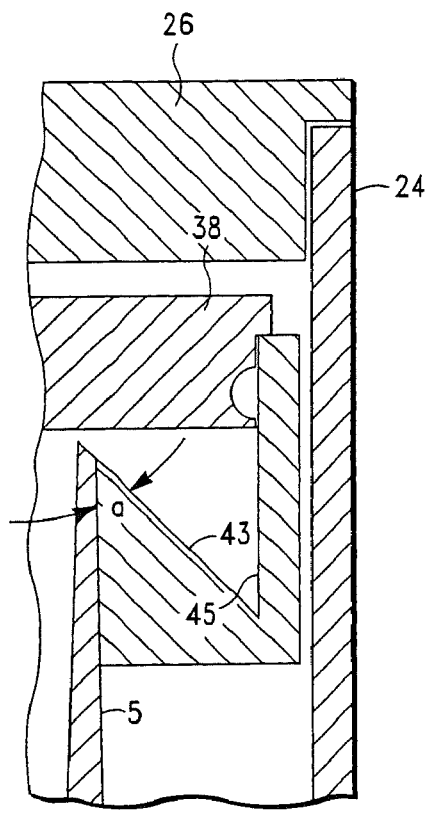
FIG. 2A is a fragmentary cross-sectional drawing of an alternative erythrocyte trap.

FIG. 2A is a fragmentary cross-sectional drawing of an alternative erythrocyte trap configuration. In this alternative embodiment, the upper surface portion 42 of the erythrocyte capture chamber 31 shown in FIG. 2 extends as surface 43 downward to the opposing wall 45, providing a continuous sloped surface for movement of platelets to the centrifugal chamber 5 during centrifugation. Surface 43 forms the angle "a" with the central axis (not shown) of the erythrocyte capture chamber.

Figure 2B:
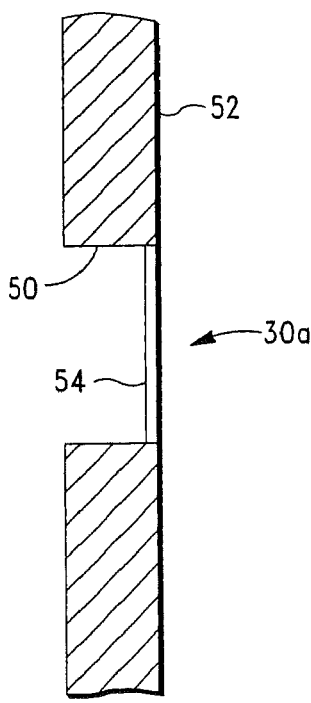
FIG. 2B is a detailed fragmentary view of a vent system according to this invention that uses a sterile porous sheet to allow air movement into and from the outer container.

FIG. 2B is a detailed fragmentary view of a vent system 30a according to this invention that uses a sterile porous sheet to allow air movement into and from the outer container. In this embodiment, an air flow passageway 50 in a wall 52 of the outer container 24 (FIGS. 1 and 2) is sealed with a conventional sterile porous sheet 54. The sterile porous sheet 54 that has sufficient porosity to allow free movement of air through the sheet, but is an effective microorganism barrier that prevents movement of microorganisms from the outer environment into the container 24. This prevents significant fluctuations of air pressure in the outer container 24 during liquid movement into and out of the system.

Figure 2C:
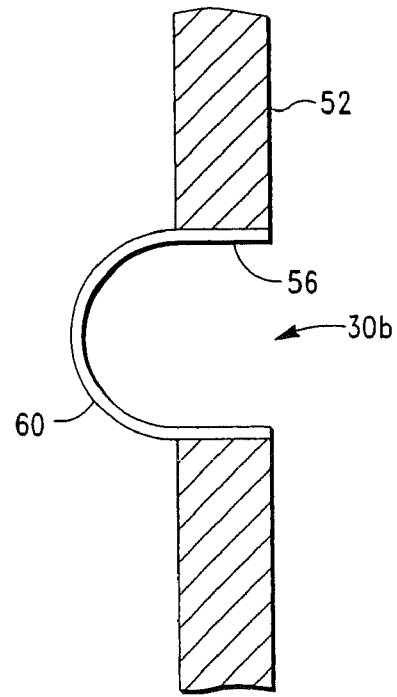
FIG. 2C is a detailed fragmentary view of a vent system according to this invention that uses a flexible balloon or diaphragm to allow air movement into and from the outer container.

FIG. 2C is a detailed fragmentary view of a vent system 30b according to this invention that uses a flexible balloon or diaphragm to allow air movement into and out of the outer container 24. In this embodiment, an air flow passageway 56 in the wall 52 of the outer container 24 (FIGS. 1 and 2) is sealed with a balloon or flexible diaphragm 60. The balloon or flexible diaphragm 60 should have sufficient flexibility and size to allow free movement of air through the air flow passageway 56 in a volume that can be at least equal to the total volume of blood that is introduced into the system during the separation process. This prevents significant fluctuations of air pressure in the outer container 24 during liquid movement into and out of the system. The balloon or flexible diaphragm 60 must have the integrity to be an effective microorganism barrier preventing movement of microorganisms from the outer environment into the container 24 during PRP removal.

FIGS. 3-5 show successive stages in the preparation of PRP with the device of FIG. 1. FIG. 3 is a schematic cross-sectional drawing of the centrifugal separator of FIG. 1 after being loaded with blood 62 from syringe 44. Syringe 44 is attached through the Luer port 28 and communicates with the access tube 29, and the plunger 46 has been depressed to expel the blood contents of the syringe into the separation chamber 2.

FIG. 4 is a schematic cross-sectional drawing of the centrifugal separator of FIG. 1 during the spin separation phase. During this phase, the syringe 44 can be removed as shown, to be replaced with a sterile cap or a fresh syringe to remove separated PRP product. Alternatively, the syringe 44 can be left in place during the separation phase (not shown) and reused to remove the PRP product. During the spin phase, the centrifugal force causes the more dense erythrocytes 64 to move outward through the plasma until they collect in the erythrocyte capture chamber, leaving PRP 66 in the centrifugal drum 5.

FIG. 5 is a schematic cross-sectional drawing of the centrifugal separator of FIG. 1 after centrifugation has ended. When centrifugation is complete and the centrifugal forces are no longer present, the dense erythrocyte layer remains isolated in the erythrocyte capture chamber 31, and the layer of PRP 66 in the centrifugal drum collects at the lowermost section of the centrifugal chamber. The PRP can then be removed through the access tube 29 from the centrifugal drum 5 with the original syringe 44 (FIG. 3) or a fresh syringe positioned as shown in FIG. 3.

Figure 6:
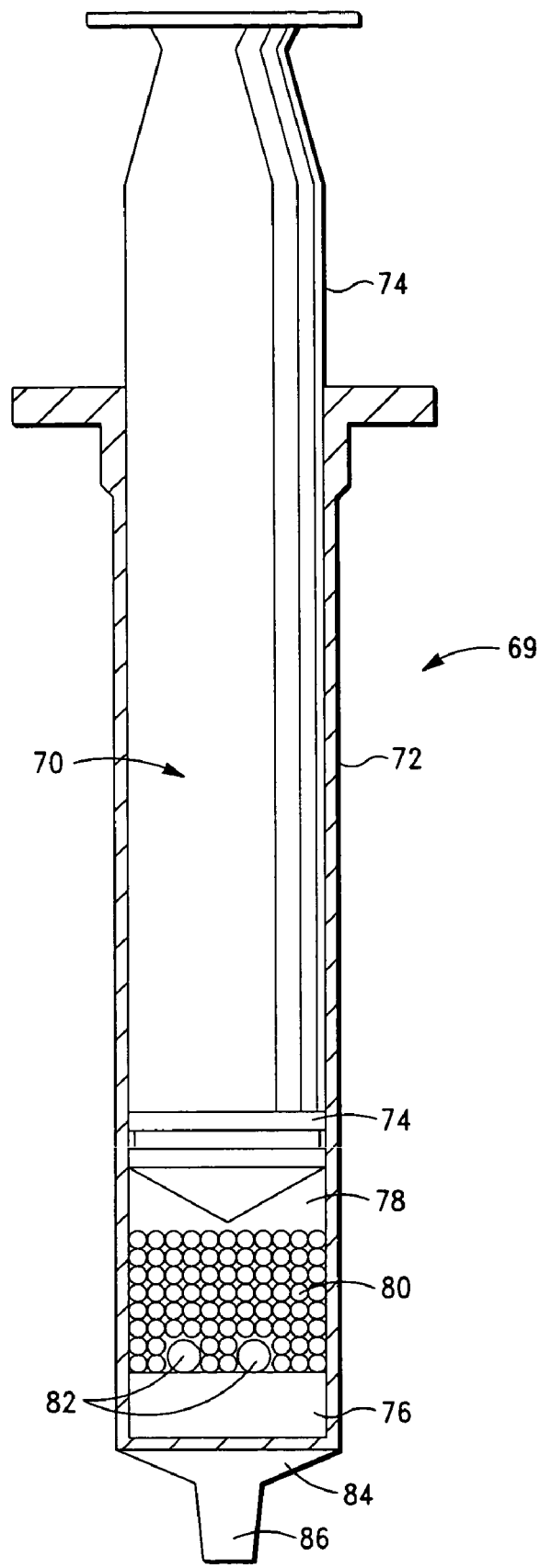
FIG. 6 is a cross-sectional drawing of a concentrator syringe.

If one desires to obtain a PRP concentrate according to this invention, one can use the concentrating syringe shown in FIG. 6 wherein FIG. 6 is a cross-sectional schematic view of a syringe embodiment for producing PRP concentrate from PRP. The syringe device 69 includes a process chamber 70 having an outer wall 72. In the process chamber 70, a plunger 74 is positioned above filter 76, the plunger 74 and the filter 76 defining a concentrating portion or chamber 78 of the process chamber 70. The concentrator chamber 78 contains concentrating desiccated hydrogel beads 80 and one or more agitators 82. A concentrate chamber 84, positioned below or downstream of filter 76, includes an inlet/outlet port 86.

The concentrating desiccated hydrogel beads 80 can be insoluble beads or disks that will absorb a substantial volume of water and not introduce any undesirable contaminant into the plasma. They can be dextranomer or acrylamide beads that are commercially available (Debrisan from Pharmacia and BIO-GEL P™ from Bio-Rad Laboratories, respectively). Alternatively, other concentrators can be used, such as SEPHADEX™ moisture or water absorbents (available from Pharmacia), silica gel, zeolites, cross-linked agarose, etc., in the form of insoluble inert beads.

The agitators 82 can be dense objects such as inert metal spheres. It will be readily apparent to a person skilled in the art that the shape, composition and density of the agitators 82 can vary widely without departing from the invention so long as the agitator has a density substantially greater than whole blood. It is advantageous that the agitator be a metal sphere such as a titanium or stainless steel sphere that will not react with blood components, or a dense sphere coated with an inert coating that will not react with blood components.

The filter 76 can be any inert mesh or porous materials which will permit the passage of plasma and prevent passage of the hydrogel beads and agitator. The filter can be a metal wire or inert fiber frit of either woven or non-woven composition, or any other frit construction which, when the liquid in the concentration chamber is passed through the filter, will permit passage of the PRP and not the hydrogel beads and agitator, effectively separating the PRP from the hydrogel beads and agitators as will be described in greater detail hereinafter.

It is important that the water removal procedure be carried out with minimal activation of the platelets and minimal denaturation of the fibrinogen. Prior art commercial procedures for preparing plasma concentrate use precipitation to separate fibrinogen from albumin and reconstitution to prepare the sealant. This deactivates a major portion of the fibrinogen and removes healing factors. As a result proportionally more of the reconstituted precipitate is required to achieve effective tissue sealing. With the device of this invention, denaturing of the fibrinogen is avoided by water removal and the healing factors in the plasma are retained with the fibrinogen during the concentration step, yielding a more effective tissue sealant and adhesive that also promotes healing.

Figure 7:
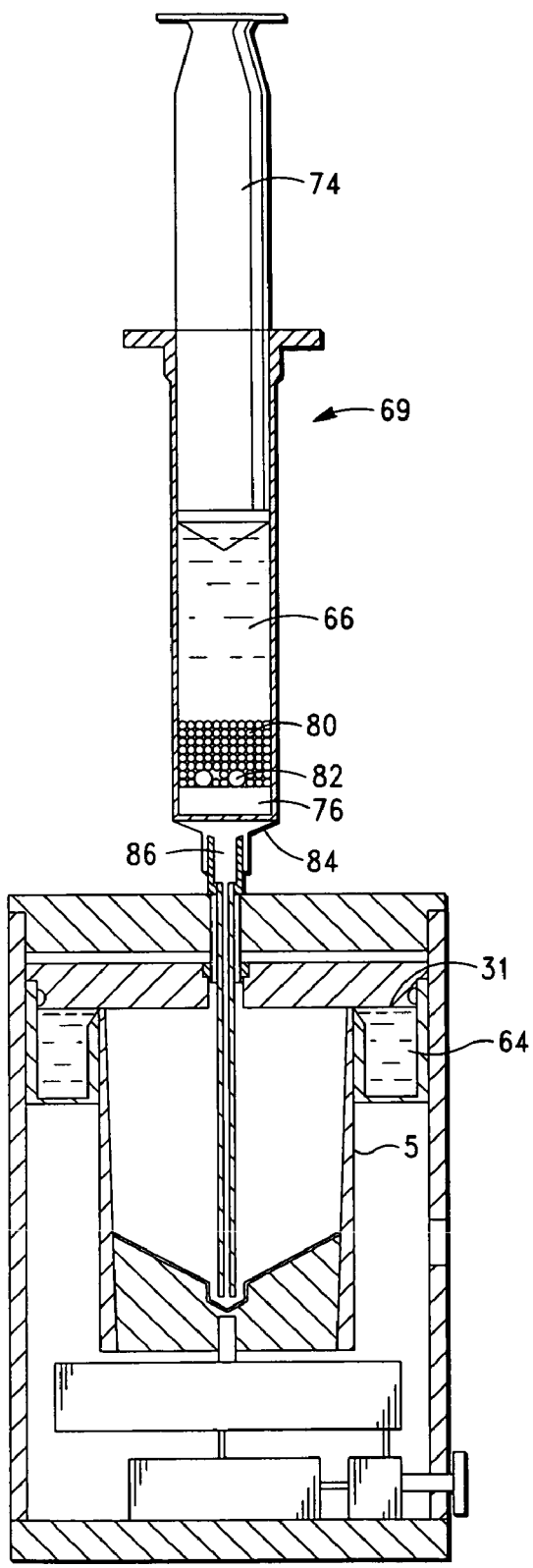
FIG. 7 a schematic cross-sectional drawing of the separation separator of FIG. 1 after PRP has been drawn into a concentrator syringe.
Figure 8:
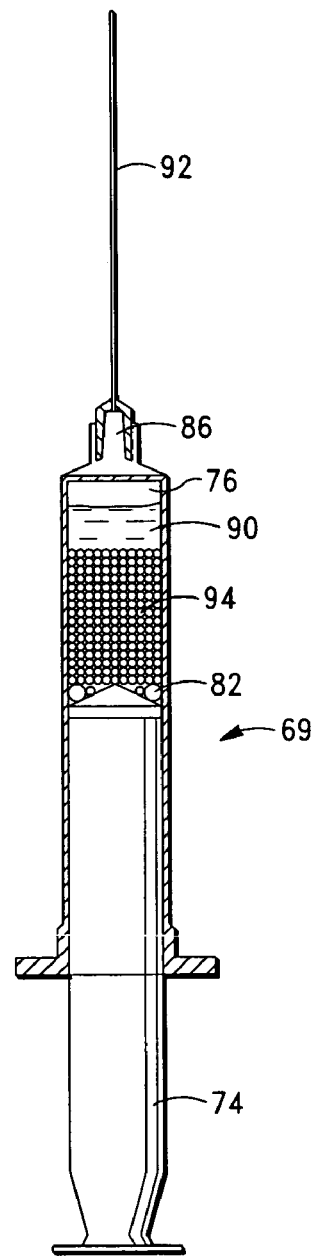
FIG. 8 shows a concentrator syringe containing PRP after the water removal phase with the PRP concentrate ready for use.

FIGS. 7 and 8 show the preparation of PRP concentrate using the syringe concentrator shown in FIG. 6. FIG. 7 is a schematic cross-sectional drawing of the centrifugal separator of FIG. 5 after PRP 66 has been drawn into a concentrator syringe, and FIG. 8 shows a concentrator syringe containing PRP concentrate 90 after the water removal phase. Moving plunger or piston 74 draws PRP 66 from the centrifugal drum 5 into the syringe chamber. A volume of air is also drawn into the syringe to facilitate expulsion of PRP concentrate after concentration.

The concentrator syringe is then withdrawn from the centrifugal separator and shaken by a reciprocal movement in the direction of the syringe axis. This movement causes relative agitating movement of the agitator balls 82 in the PRP 66, stirring the hydrogel beads in the solution, and mixing the PRP to reduce localized concentrations and gel polarization of plasma proteins around the bead surfaces, thereby facilitating movement of water from the PRP into the beads 80. FIG. 8 shows the concentrator syringe with the PRP concentrate 90 after the water removal step is completed. Movement of the plunger 74 toward the inlet-outlet port 86 discharges PRP concentrate 90 through the applicator needle 92, the filter 76 preventing movement of the hydrated beads 94 and agitator 82 with the PRP concentrate. Concentrated PRP retained within the interstitial space between beads is purged by air as the plunger is depressed further.

Figure 9:
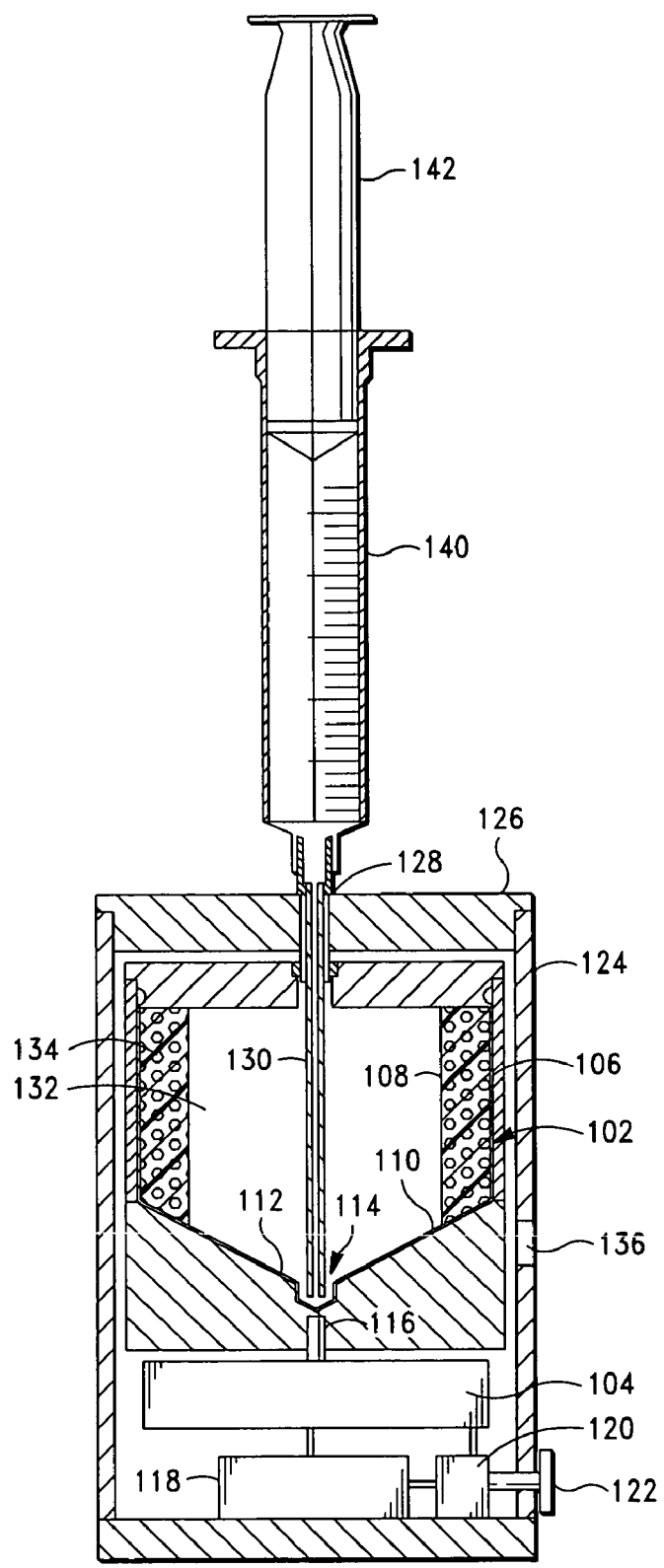
FIG. 9 is a schematic cross-sectional drawing of a separation separator of this invention with a depth filter erythrocyte trap.

FIG. 9 is a schematic cross-sectional drawing of a centrifugal separator of this invention with a depth filter erythrocyte trap. This embodiment also comprises a centrifugal separator unit 102 and a motor 104. The centrifugal separator unit comprises a centrifugal drum 106 having an inner wall surface 108 with a bottom edge 110, a drum bottom 112, and a central axis (not shown). The drum bottom 112 has a central depression 114, the bottom 112 constituting a floor sloping downward from the lower edge 110 to the central depression 114. The motor 104 has a drive axis 116 coaxial with the central axis. The motor 104 has the capacity to rotate the centrifugal drum 102 at a speed of at least 2,000 rpm for 120 seconds with a total power consumption of less than 500 mAh, the power that is obtainable from a small battery such as a conventional 9 volt alkaline battery.

The complete, self-contained unit includes a battery 118 connected to the motor 104 through conventional power connections. The battery 118 has the capacity to provide sufficient power to complete the separation process and being connected to the motor through an on/off toggle or timer switch 120 with a manual knob 122.

An outer container 124 encloses the centrifugal separation unit. The container 124 has a top 126 with a sterile syringe port 128 aligned with the central depression 114, an access tube 130 connected to and extending downward from the syringe port 128 for introducing blood into the separation chamber 132 and for removing PRP from the separation chamber 132 as is explained in greater detail with respect to FIGS. 10-13 hereinafter.

The inner wall 108 of the centrifugal separator unit 102 is the surface of a depth filter 134 having pores sized to capture erythrocytes moving into the pores during centrifugal separation of the erythrocytes from blood and to retain the erythrocytes in the material of the depth filter when centrifugal separation is completed, the material of the depth filter being selected from a material that does not significantly activate platelets contacting the surface thereof.

The depth filter 134 can be a honeycomb-like or woven fiber material that allows fluids and small particles to flow freely (e.g., felt or open cell polyurethane foam). Like a wetted sponge, the depth filter holds liquid against a certain head of pressure due to surface tension forces. Thus, blood cells or other suspended particulates remain entrapped within the foam when the centrifuge stops and separated platelet-rich plasma drains from the surface under the force of gravity. Foam can be either rigid or flexible and can be formed into the appropriate annular shape for the device by molding or die-cutting. The parts are sized so that the packed cell (e.g., erythrocyte and leukocyte) layer is fully contained within the outer depth filter chamber, which retains the cells when the centrifuge stops.

With this device, erythrocytes moving outward through the plasma during centrifugation pass into and are captured by the depth filter 134, and the PRP flowing downward when centrifugation is ended is substantially free from erythrocytes as is described hereinafter in greater detail with respect to FIGS. 10-13.

Similar to the vent system provided in the system shown in FIGS. 1 and 2, a vent system 136 can be provided in the outer container 124. This vent system can be the same as described hereinabove with respect to FIGS. 2B and 2C.

FIG. 10 is a schematic cross-sectional drawing of the centrifugal separator of FIG. 9 after being loaded with blood 138 from syringe 140, the syringe connecting through the sterile seal 128 and into the vertical tube 130, and the plunger 142 having been depressed to expel the blood contents of the syringe into the separation chamber 132.

FIG. 11 is a schematic cross-sectional drawing of the centrifugal separator of FIG. 10 during the spin separation phase. During this phase, the syringe 140 can be removed as shown to be replaced with a sterile cap or fresh syringe to remove the separated PRP product. Alternatively, the syringe 140 can be left in place (not shown) during the separation phase and used to remove the PRP product. During the spin phase, the centrifugal force causes the more dense erythrocytes to move outward through the plasma into the depth filter 134, leaving PRP 148 substantially free from erythrocytes in the centrifugal drum 102.

FIG. 12 is a schematic cross-sectional drawing of the centrifugal separator of FIG. 11 after centrifugation has ended. When centrifugation is complete and the centrifugal forces are no longer present, the erythrocyte-free PRP product 148 flows downward in the separator chamber 132, the erythrocytes remaining trapped in the depth filter 134. The PRP 148 that collects in the centrifugal drum 102 is substantially free from erythrocytes and leukocytes. The PRP 148 can then be removed from the centrifugal drum 102 with the original syringe 140 (FIG. 10) or a fresh syringe as will be readily apparent to a person skilled in the art.

FIG. 13 is a schematic cross-sectional drawing of the centrifugal separator of FIG. 12 after PRP 148 has been drawn into a concentrator syringe 69. Withdrawing the plunger or piston 74 draws PRP 148 from the centrifugal chamber 132 into the syringe barrel 150.

The water is removed from the PRP 148 to produce a PRP concentrate and expelled from the syringe as is described hereinabove with respect to FIGS. 7 and 8.

FIG. 14 is a schematic representation of a combination centrifugal separator and hollow fiber concentrator of this invention. The entire separation and concentration components are enclosed in a housing 160. The top of the housing has a sterile vent 162 to allow passage of air displaced during addition and removal of fluid from the device and a Luer fitting 164 to which a standard syringe 166 with a piston 168 and piston actuator 170 can be coupled.

A centrifugal separator 172 can have the annular erythrocyte trapping system shown and described hereinabove with respect to FIGS. 1-5 or it can have the depth filter erythrocyte trapping system shown and described hereinabove with respect to FIGS. 9-13.

A drive motor 174 is positioned in the bottom section of the housing 160 below the centrifugal separator 172 in the basic configurations shown in FIGS. 1 and 9.

Positioning the hollow fiber concentrator system 176 above the centrifugal separator 172 simplifies the liquid transfer components of the concentrator, although it will be readily apparent to a person skilled in the art that alternative configurations such as side-by-side placement or placing the centrifuge above the concentrator are also suitable, provided adequate space is provided to house the fluid transfer tubing.

The concentrator system comprises a hollow fiber cartridge 178 and a pump 180.

A central tube 182 having outlet 184 extends from the Luer fitting 164 toward the depression 186 at the bottom of the centrifugal separator 172. A inlet flow check valve 188 limiting liquid flow toward the centrifugal separator is placed in the central tube 182 at an intermediate level The tube outlet 184 is positioned to circulate PRP, preferably stopping short of the bottom 186.

A return tube 190 extends from the bottom depression 186 to a pump inlet check valve 192 communicating with the inlet of pump 180. Check valve 192 directs liquid movement in the direction toward the pump, thus preventing backflow into line 190. A second return tube, but also referred to as a line or conduit, 194 extends from pump outlet check valve 196 communicating with the outlet of pump 180. Check valve 196 directs liquid movement in the direction leading away from the pump, thus preventing backflow from line 194 to the pump. Second return tube 194 extends to the inlet manifold 198 of the hollow fiber cartridge concentrator 178. A third return tube 200 extends from the outlet manifold 202 of the hollow fiber cartridge 178 to a concentrator outlet check valve 204 leading to the central tube 182 at a position above (or upstream of) check valve 188. Tube 200 is sized to restrict the flow of fluid, generating a backpressure upstream in the fluid circulation path to drive filtration through the hollow fiber membranes. Check valve 204 prevents backflow of liquid from the tube 182 to the hollow fiber cartridge 178.

The hollow fiber cartridge includes fiber membranes that efficiently remove water and salts from the plasma while leaving larger healing factors. Choice of the fiber materials and pore distributions is a critical factor because rapid water removal without significant platelet damage must be achieved. The large concentration of protein present in plasma presents another difficulty since it thickens along the membrane surface due to localized concentration and gel polarization. Therefore, the fiber membranes and their configuration must facilitate sweeping of the membrane surface by passing plasma, disrupting the polarization and redistributing the plasma constituents. Furthermore, because a preferred embodiment of this device is intended to be self-contained and highly portable, it is preferred that the hollow fiber cartridge provide its ultrafiltration function with minimal energy consumption so that complete separation and concentration can be achieved with a standard small (e.g., 9 volt transistor) battery.

The pump 180 can be a conventional piston or diaphragm pump that provides the necessary circulation of plasma through the hollow fiber concentrator system 176 without use of excessive energy. Preferably, the pump 180 should have the capacity to complete concentration of the plasma with a power consumption of less than 500 mAh, that is, the power available from a small battery such as a standard 9 volt alkaline battery.

Power to the motor 174 and pump 180 is provided by conventional wiring and a small battery (not shown) that has the capacity to provide sufficient power to complete the concentration process. A small (e.g., standard 9 V transistor radio) battery is acceptable. Alternatively, if the unit is to be used in a location with standard auxiliary power, a conventional power supply system using standard business and residential power can be used.

The system shown in FIG. 14 operates as follows: Blood is provided to separator Luer fitting by a blood-filled syringe, using syringe such as syringe 166. Downward movement of the actuator 170 moves the piston 168 in a downward direction, expelling the contents of the syringe through the Luer fitting 164 and the tubing 182 through the inlet check valve 188 into the bottom of the centrifugal separator 172. After its contents have been expelled, the syringe can be left in place or replaced with a fresh syringe or sealing cap to prevent fluid from escaping through the Luer port 164 during the concentrating step of the process.

Operation of the centrifugal separator 172 removes erythrocytes and leukocytes from the blood, leaving PRP in the bottom of the centrifuge chamber after centrifugation is stopped.

Operation of the pump 180 draws PRP from the lower depression 186 of the centrifugal separator upward through tube 190, through the pump inlet check valve 192 into the pumping chamber (not shown) of the pump 180. Then PRP flows through pump 180 and through pump outlet check valve 196. From check valve 196, the PRP passes through the tubing 194 into the inlet manifold 198 of the hollow fiber concentrator 178 and through the hollow fiber concentrator.

PRP from which a portion of the water and salts have been removed then flows from the outlet manifold 202 of the hollow fiber concentrator 178 through flow restrictive tubing 200 and concentrator outlet check valve 204 to the inlet tubing 182, and then through check valve 188 to the bottom of the centrifugal separator 172 where it mixes with the other PRP. This cycling process is continued, removing a portion of the water in each pass, until the desired concentration of PRP has been obtained.

With the device of this invention PRP erythrocyte removal and concentration of the PRP to a platelet concentration of 3× can be automatically achieved within 5 minutes. If higher PRP concentration is needed for a particular application such as for sealing tissues to stop bleeding, the concentration cycle can be continued beyond 5 minutes, whereby concentration up to 5× and higher can be achieved.

FIG. 15 is a schematic cross-sectional view of a hollow fiber concentrator shown in FIG. 14, and FIG. 16 is a cross-sectional view of the hollow fiber concentrator of FIG. 15, taken along the line 16-16.

Referring to FIG. 15, the hollow fiber concentrator 178 is combined with an extracted liquid reservoir 206. The concentrator 178 has an outer housing 208 that encloses the inlet manifold 198, an outlet manifold 202, a plurality of hollow ultrafiltration fibers 210 and an extracted liquid chamber 212. Each of the hollow fibers 210 has a wall 214, an axial passageway 216, an inlet end 218 and an outlet end 220. The inlet end 218 of each hollow fiber 210 is secured to a correspondingly sized hole in the inlet manifold plate 222 in a conventional manner that establishes communication between the hollow fiber passageway 216 and the inlet manifold 198 while preventing escape of the liquid contents thereof into the extracted liquid chamber 212. The outlet end 220 of each hollow fiber 210 is secured to a correspondingly sized hole in the outlet manifold plate 226 in a conventional manner that establishes communication between the hollow fiber passageway 216 and the outlet manifold 202 while preventing escape of the liquid contents thereof into the extracted liquid chamber 212.

Referring to FIGS. 15 and 16, the extracted liquid chamber 212 is the space defined by the inner wall surface 213 of the housing 208, the outer wall surface of the hollow fibers 210, and the manifold plates 222 and 226. The extracted liquid chamber 212 captures the liquid that passes through the hollow fibers 210 in the ultrafiltration process.

The outlet end of conduit 194 shown in FIG. 14 connects with the inlet manifold 232 through manifold inlet conduit 230. The inlet end of conduit 200 shown in FIG. 14 connects with the outlet manifold 202 through manifold outlet conduit 228.

During the water removal process, pressurized plasma passes from conduit 194 through the inlet manifold inlet conduit 230 into the inlet manifold 198, and then through the hollow fibers 210. In each pass a portion of the water and salts passes through the pores in the fiber walls into the extracted liquid chamber 212. The concentrated plasma then passes into the outlet manifold 202, through the outlet manifold outlet conduit 228 and then to the conduit 200.

The extracted liquid reservoir 206 has a reservoir housing 234 that connects with an overflow conduit 236. The overflow reservoir 206 has an air vent 238.

FIG. 17 is a schematic cross-sectional view of the membrane valve air vent 238 in the hollow fiber concentrator of FIG. 15. The valve 238 comprises a porous lower hydrophilic membrane 240 communicating with the interior of the extracted liquid reservoir 206 and a porous upper hydrophobic membrane 242 that communicates with outer space surrounding the reservoir. The extracted liquid reservoir captures extracted liquid when the volume of the extracted liquid exceeds the volume of the extracted liquid chamber 213 and the excess liquid escapes through the extracted liquid conduit 236 into the extracted liquid chamber 206. Air in the extracted liquid chamber displaced by the incoming liquid escapes through the porous membranes 240 and 242 until the liquid level reaches the membranes, saturating the hydrophilic membrane 140. Escape of the extracted liquid from the extracted liquid chamber 206 is prevented by the hydrophobic membrane 242.

The valve prevents movement of air into the system when PRP concentrate is removed as follows. Movement of PRP concentrate from the centrifugal separator 172 (FIG. 14) creates a partial vacuum in the system. Movement of air through the valve 238 in response to this partial vacuum is prevented by the liquid saturated hydrophilic membrane 240.

Figure 18:
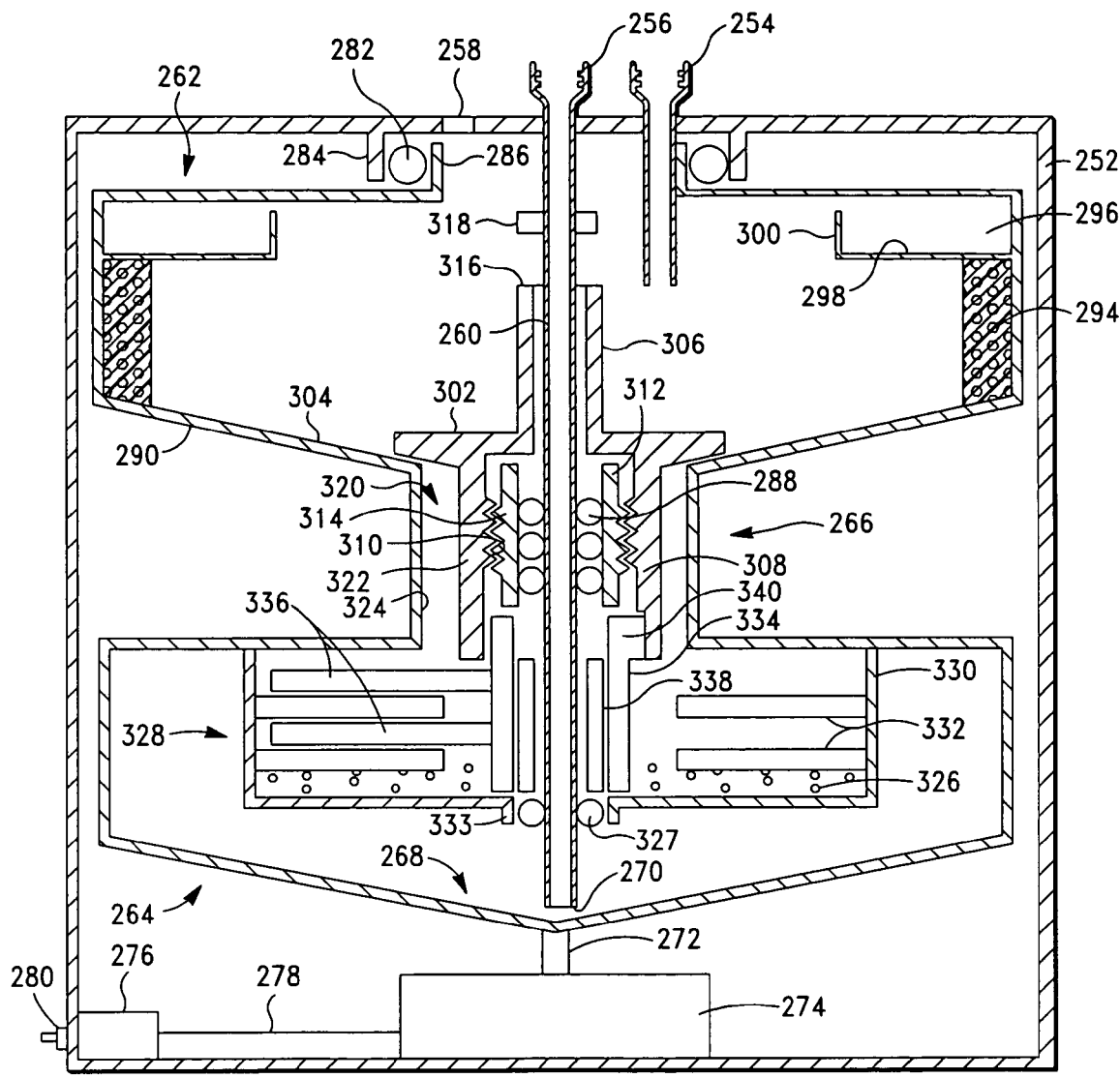
FIG. 18 is a schematic cross-sectional drawing of an automated spring-clutch system for preparing PRP concentrate from a patient's blood.

FIG. 18 is a schematic cross-sectional drawing of an automated spring-clutch system for preparing PRP concentrate from a patient's blood. Like other embodiments of this invention, the disposable, single-use system is enclosed in a compact portable device that can be smaller than a twelve ounce soft drink can.

Referring to FIG. 18, the outer housing 252 is sealed except for the blood inlet port 254, the PRP concentrate withdrawal port 256, and sterile vent 258. The PRP withdrawal port 256 is one end of a rigid PRP concentrate withdrawal tube 260 that is secured to the outer housing 252 and functions as a central axle around which the rotary separation components turn and also as a PRP concentrate withdrawal tube. The separation components comprise a upper rotary centrifugal separator housing 262 and a lower rotary water removal system housing 264, these two housing being connected by an integral cylindrical waist element 266 into a unitary housing structure. The water removal system housing 264 includes a PRP concentrate reservoir 268 that communicates with the lower opening 270 of the PRP concentrate withdrawal tube 260.

The rotary components are supported on the drive axle 272 of the two direction, two speed motor 274. The direction and speed of the motor 274 are controlled by the conventional motor controller 276 to which it is connected by electrical conduit 278. Switch 280 activates the motor controller 276.

The relative position of the rotary components in the outer housing 252 is maintained by a roller bearing raceway structure. This structure that includes a plurality of roller bearings 282 positioned between an outer ring flange 284 secured to the outer housing 252 and an inner ring flange 286 secured to the upper rotary centrifugal separator housing 262.

The centrifugal blood separating components housed in the upper housing 262 of the rotary assemblage is similar in structure and function to other blood separators described hereinabove with respect to FIGS. 9-13 in that the cylindrical rotary centrifugal separator 290 has the inner surface of its outer wall lined with a cylindrical depth filter 294. A blood overflow reservoir 296, defined by a floor 298 and an integral wall 300, can function to control or limit the volume of blood that is subject to the separating operation. The overflow reservoir 296 can assist if the volume introduced exceeds the volume that can be effectively concentrated in the water removal operation, described in greater detail hereinafter. When the centrifugal separator spins during the separation phase, excess blood flows upwardly along the wall 300 and into the reservoir 296. When the separation phase ends and the rotary speed slows, the wall 300 prevents escape of liquid as it settles on the floor 298.

Suitable depth filter materials have been described hereinabove with respect to FIGS. 9-13. Alternatively, the depth filter structure 294 and overflow reservoir structure 296 can be replaced with an erythrocyte trap and function such as is described with respect to FIGS. 1-8 hereinabove in a manner that would be readily apparent to a person skilled in the art.

During the centrifugal separation stage, erythrocytes separating from the plasma flow into the depth filter 294, leaving a layer of PRP behind outside the depth filter.

When the centrifugal separation is completed and centrifugal separation is ended, the PRP flows to the bottom of the centrifugal separator where it is held by the seal of the valve plate 302 against the floor 304 of the separation housing.

The seal of the valve plate 302 against the floor 304 is opened by action of a spring clutch assembly. The valve plate 302 is a part of a valve assembly including a hollow upper valve stem 306 (a cylinder) integral with the plate 302 through which the rigid tube 260 extends. This stabilizes orientation of the valve assembly on the rigid tube 260. The lower part of the valve assembly is outer cylinder 308 with internal threads 310.

The outer cylinder 308 further encloses an inner cylinder 312 that has external threads 314 engaging the internal threads 310 of the outer cylinder 308 in sliding engagement. The spring clutch 288 wraps around the rigid tube 260 and is positioned between the inner cylinder 312 to which it is secured and the rigid tube 260. The spring clutch 288 functions as a slip bearing between the rotating internal threaded element 312 and the rigid tube 260 during the centrifugal separation phase because the direction of the movement of the spring around the rigid tube 260 tends to open the spring, reducing then sliding friction.

After the centrifugal separation of the PRP is completed, the motor 274 is then activated to turn slowly in a reverse direction. The spring-clutch 288 rotates around the rigid tube 260 in a direction that tightens the spring, locking the spring to the rigid tube 260. As the outer cylinder 308 turns around the locked stationary inner cylinder 312, the outer cylinder 308 rises, lifting unseating the valve plate 306, the movement continuing until the top surface 316 of the upper valve stem 306 abuts the collar 318 secured to the rigid tube 260.

When the valve plate 302 unseats, the PRP in the bottom of the centrifugal separator 290 flows downward through a channel 320 defined by the outer surface 322 of the lower cylinder and the inner surface 324 of the waist cylinder 266 into the lower rotary water removal system enclosed in the lower housing 264 where it contacts the desiccated gel beads 326. Direct flow of liquid from the water removal system is prevented by O-ring seal 327.

The lower rotary water removal system 328 enclosed in lower housing 264 comprises a rotary cylindrical screen element 330 which has radially inwardly extending comb elements 332 and a rake system. The bottom of the lower housing 264 has a central opening with a downwardly extending cylindrical flange 333 to accommodate the rigid tube 260. O-ring 327 is positioned between flange 333 and the rigid tube 260 to prevent liquid flow therebetween. The rake system comprises a rake cylinder 334 having radially outward extending rake elements 336 that mesh with the comb elements 332. The rake cylinder 334 is separated from the rigid tube 260 by roller bearings 338 that reduce friction between the rake cylinder 334 and the tube 260 during the high speed rotation of the centrifugation step. The rake cylinder has a projecting spline 340 that engages a matching vertical recess grove (now shown) in the lower valve stem outer cylinder 308. The spline 340 is positioned to move up and down in the matching grove to maintain engagement of the rake cylinder 334 and the lower valve stem outer cylinder 308 at all elevations of the valve stem. The spline system locks the rake cylinder 334 to the stationary tube 260 when the spring clutch engages, preventing rotation of the rake cylinder when the comb elements are rotated through the rakes.

As water is removed from the PRP by the desiccated beads 326, gel polarization occurs, slowing water absorption into the beads. To reverse this effect, the beads are slowly stirred during the dewatering process from slow rotation of the cylindrical screen and rake elements by the motor 274. The relative movement of the rake 336 through the gel beads 326 and through the spaces of the comb 320 stirs the beads and breaks up bead clumps, increasing efficiency of the water removal process. This process is obtained as follows.

When water removal is completed, the motor controller 276 can reverse rotational direction of the drive shaft 272, causing disengagement of the spring clutch 288 from the rigid tube 260, and permitting the separation assembly elements to rapidly spin as a unit. During this spin, the concentrated PRP is spun from the beads 270 through the cylindrical screen 330 where it is collected in the PRP concentrate reservoir 268. PRP concentrate is then drawn from the PRP concentrate reservoir 268 though the rigid tube 260 and out through the PRP concentrate withdrawal port 256.

Figure 19:
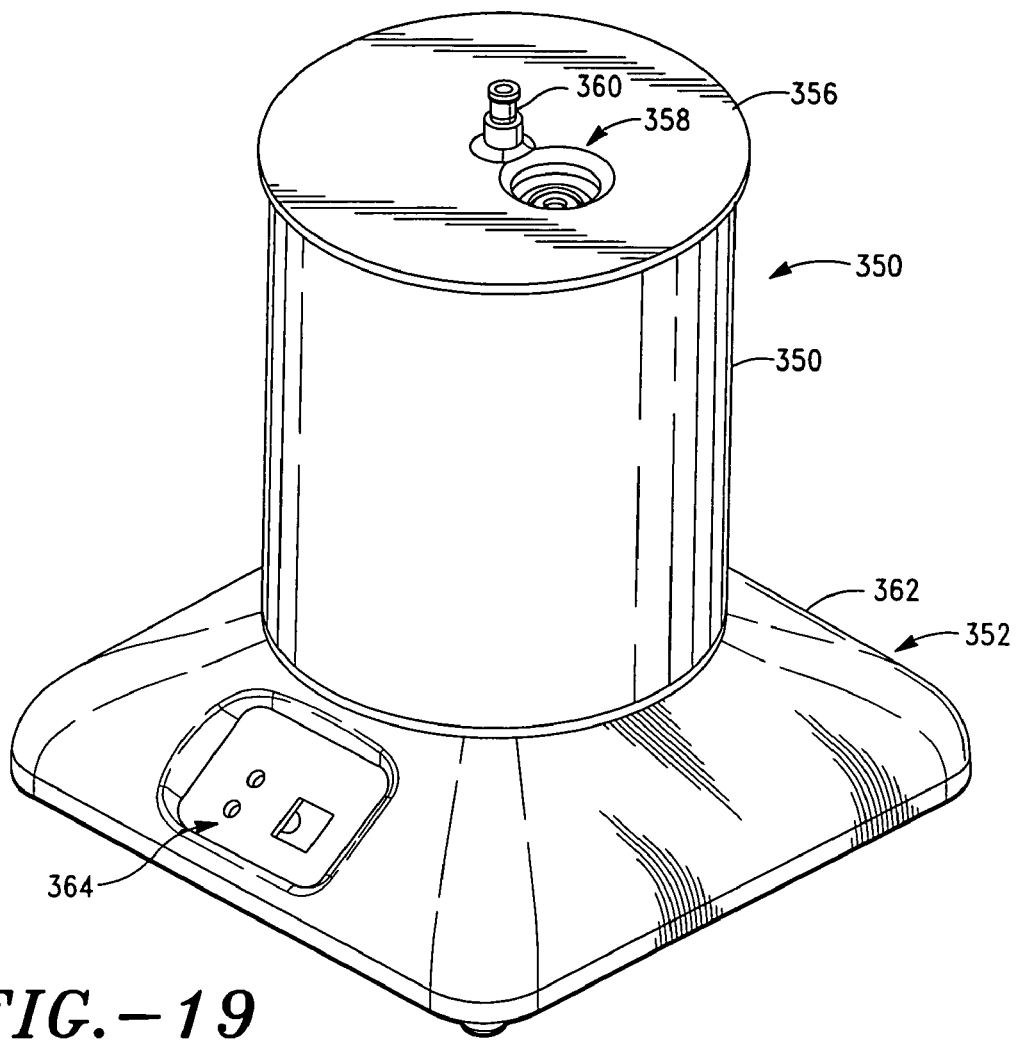
FIG. 19 is an isometric view of a plasma separator and concentrator embodiment of this invention.
Figure 20:
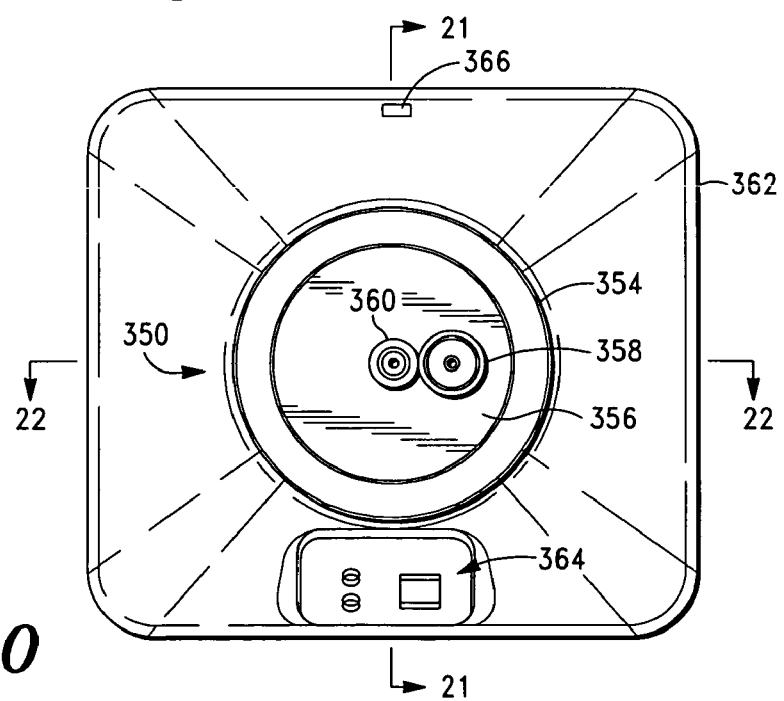
FIG. 20 is a top view of the plasma separator and concentrator shown in FIG. 19.

FIG. 19 is an isometric view of a plasma separator and concentrator embodiment of this invention; and FIG. 20 is a top view of the plasma separator and concentrator shown in FIG. 19. This embodiment comprises a disposable separator/concentrator module 350 and a permanent base 352 with the motor and control system. The separator/concentrator module 350 has a housing 354 and a housing top 356. The housing top 356 has a blood inlet port 358 and a plasma concentrate outlet port 360. The base 352 has a base housing 362 with a control switch 364 and an external power connector 366 (FIG. 20). This compact unit separates platelet rich plasma (PRP) from blood and removes water from the PRP to form an autologous platelet rich plasma concentrate from a patients blood within minutes.

FIG. 21 is a cross-sectional view of the plasma separator and concentrator of FIG. 20, taken along the line 21-21, separated along the vertical axis to show the motor drive and drive receptor relationship prior to placing the disposable separator-concentrator assembly on the drive base. The drive base 368 comprises a base housing 370 supported on a plurality of base feet 372. The housing has a rotary assembly guide surface 374 that is shaped to match the shape of the base receptor 376 of the separator and concentrator assembly 350. It has an annular support surface 380 that together with the top support surface 382 supports and aligns the separator and concentrator assembly 350 on the base 368. In the base 368, a motor 384 is mounted on a support plate 386 that is held in position by a plurality of support fixtures 388. The motor 384 has a drive connector 390 that securely mates with the rotary assembly drive receptor 392. The base has a conventional power connector 366 and a conventional motor control switch 364 that are electrically connected to the motor with conductors in a conventional manner (not shown). The motor control switch 364 includes a conventional timer that controls the motor speed at different phases of the separation and concentration process as is described in greater detail hereinafter.

The rotary unit comprises the housing 354 with the housing top 356 supporting the PRP concentrate outlet port 360. The housing 354 includes a base 394 with a base receptor 376 that is shaped and sized to mate with the top support surface 374 and assembly guide to support and align the separator and concentrator assembly 350 on the base 374. Axially concentric bearing assembly 396 is positioned to support the separator and concentrator assembly 350 in position to permit mating of the drive connector 390 and the drive receptor 392. The drive connector 390 and drive receptor 392 have matching shapes that require the two units to turn a single unit. They can have any cross-sectional shape that prevents the drive connector 390 from turning inside the drive receptor 392 such as the rectangular shape shown. It can also have any other polygonal or oval shape that provides this result. Circular cross-sections are also acceptable if they are keyed in a conventional manner fully within the skill of the art, and all functionally equivalent shapes are intended to be within the scope of this invention.

The separation and concentration assembly 378 rotates about the vertical axes established by the stationary fixed tube 398. Tube 398 also constitutes a PRP concentrate conduit. This communicates with the PRP concentrate outlet 360. Tube 398 is rigidly secured against rotation about its central axis by its connection with the top 356 of the outer housing 354. The lower end 398 of the tube 398 includes a PRP concentrate inlet 400 and a rake hub 402 that is rigidly connected to the tube so that it remains stationary when the rotary components are in motion as will be described in greater detail hereinafter.

The separation and concentration assembly 378 includes a rotary housing 378, the tapered bottom 404 of which includes the drive receptor 392. The separation and concentration assembly 378 has a top plate 406 with a sterile vent 408 that is supported in its position on the tube 398 by sleeve bearing 410.

Figure 22:
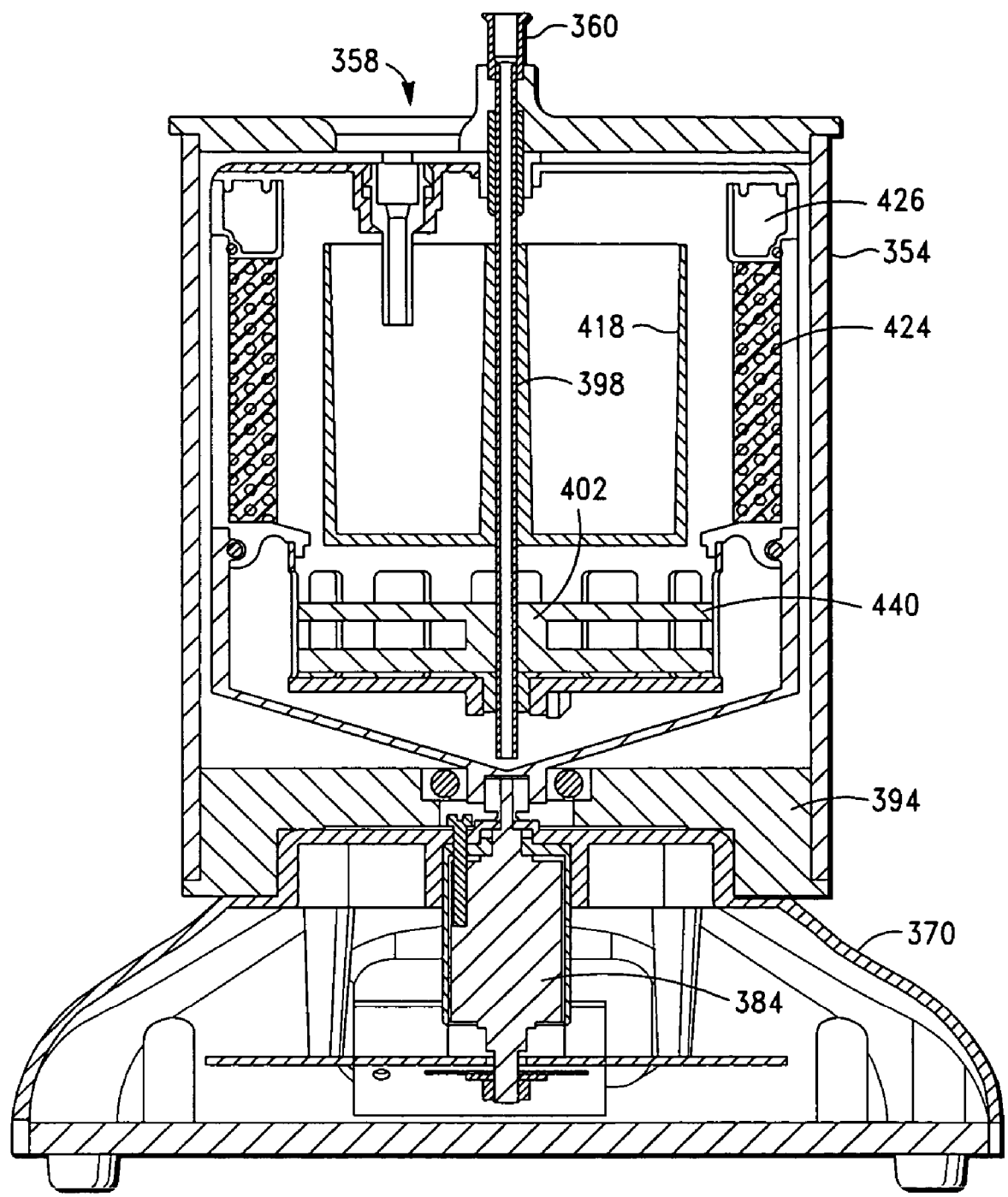
FIG. 22 is a cross-sectional view of the plasma separator and concentrator of FIG. 20, taken along the line 22-22.
Figure 23:
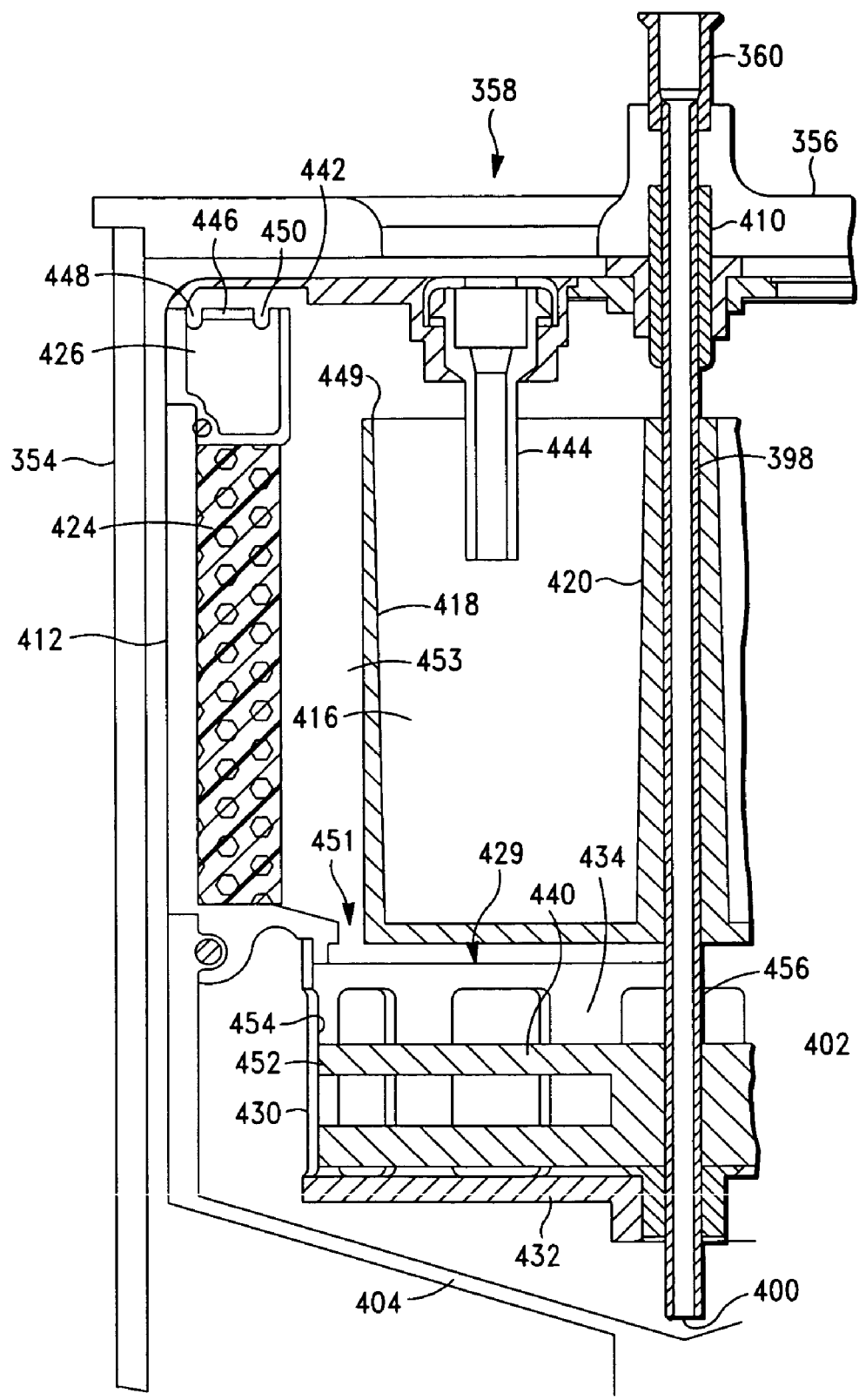
FIG. 23 is a fragmentary cross-sectional view of the separator-concentrator shown in FIG. 22.

The desiccated gel beads used to removed water from the PRP are omitted from FIGS. 21-23 to present more clearly the other components of the concentrating assembly. They are shown in FIGS. 24-27.

The separation and concentration assembly 378 has an outer wall 412 that isolates the blood components during the separation and concentrating process. The upper portion of the housing 378 encloses a centrifugal plasma separator that comprises a cylindrical blood reservoir 416 with an outwardly tapering inner surface 418 and an inner wall 420 that surrounds the tube 398 and is configured to permit free rotation of the inner wall 420 around the tube 398. This combination maintains axial orientation of the blood reservoir during centrifugal motion of the separation process. Surrounding the blood reservoir 416 is a cylindrical depth filter 424 above which is positioned an annular blood overflow reservoir 426, details and functions of which are described in greater detail hereinbelow with respect to FIG. 23.

A concentrator assembly 428 is positioned below the blood reservoir 416 and depth filter 424. The concentration assembly comprises a concentrating basket 429 formed by an axially concentric rotary screen 430 and a concentrator base 432. The screen has a cylindrical cross-section and is supported by a circular array of vertical supports 434. Surrounding the screen 430 is a concentric PRP concentrate reservoir comprising a vertical side wall 438 and the tapered bottom 404. The center of the tapered bottom 404 is positioned adjacent the inlet opening 400 of the tube 398.

FIG. 22 is a cross-sectional view of the plasma separator and concentrator of FIG. 20, taken along the line 22-22 and should be considered together with FIGS. 21 and 23 to form a complete understanding of the structure of the invention. The view provided by this figure shows, in addition to features described above with respect to FIG. 21, a cross-sectional view of the blood inlet 358 supported by the housing top 356 and the rake elements 440 mounted on the rake hub 402.

FIG. 23 is a fragmentary cross-sectional view of the separator-concentrator shown in FIG. 22. A top plate 442 is secured to the top of the outer wall 412 to confine the blood to the separator during the centrifugal separation. The top plate 442 supports a blood distribution tube 444 that is positioned below and in alignment with the blood inlet port 358 at the first stage when blood is introduced into the separator.

The annular blood overflow chamber 426 has a top plate 446 with a blood flow inlet opening 448 adjacent the top plate 442 and a second vent opening 450 that is radially inward from the blood inlet opening. This allows overflowing blood to enter the chamber during the centrifugal separation phase through the first inlet opening 448 and allows escape of air displaced by the blood through the second vent opening 450.

The tapered outer wall 418 of the blood reservoir has a tip edge 449.

A PRP flow passageway 451 leads from the outer separation chamber 453 to the concentrator basket 429.

The rakes 440 have a terminal tip edge 452 that are positioned adjacent the inner surfaces 454 of the upright screen supports 434 so they closely sweep the surfaces 454 during their rotation. The upright screen supports 434 have a thickness and openings 456 into which gel beads collect during the fast centrifuge phase, placing them beyond the tip edge of the rakes.

The screen 430 has a mesh size that is sufficiently small to prevent escape of the gel beads from the chamber concentration chamber during the final centrifugal separation of the PRP concentrate from the gel beads.

Figure 27:
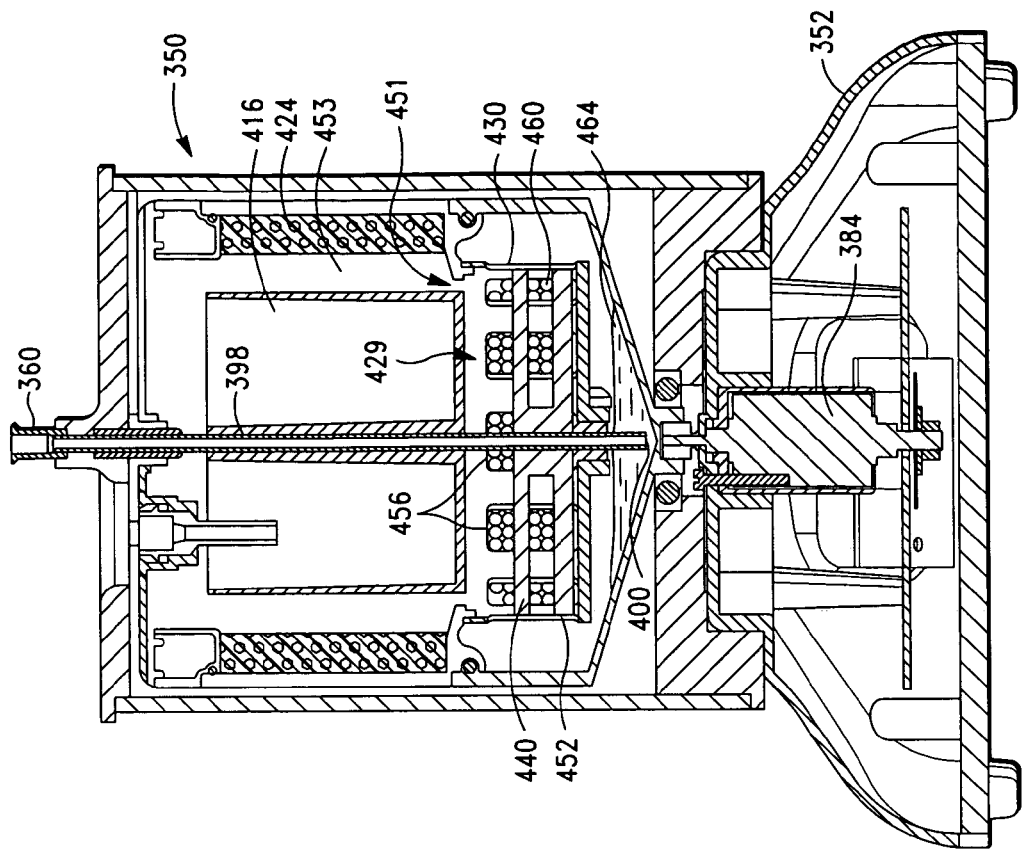
FIG. 27 is a cross-sectional drawing of the device of FIGS. 19-23 during the centrifugal PRP concentrate separation stage.
Figure 26:
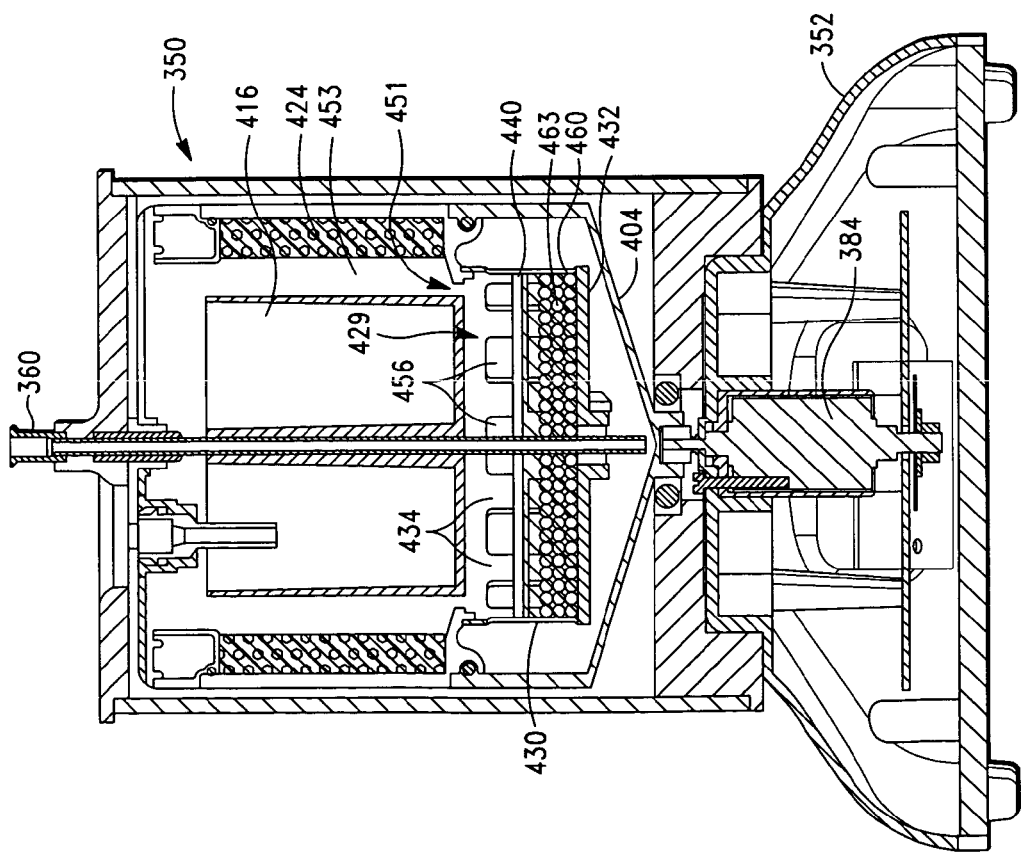
FIG. 26 is a cross-sectional drawing of the device of FIGS. 19-23 during the slow rotation concentration stage.

FIGS. 24-27 illustrate the device of FIGS. 19-23 during the phases of the blood separation and concentration. FIG. 24 is a cross-sectional drawing of the device of FIGS. 19-23 after blood has been added, FIG. 25 is a cross-sectional drawing of the device during the centrifugal separation stage producing PRP, FIG. 26 is a cross-sectional drawing of the device during the slow rotation concentration stage, and FIG. 27 is a cross-sectional drawing of the device of during the centrifugal PRP concentrate separation stage.

The blood separation and concentration with the device of this invention proceeds as follows:

Referring to FIG. 24, a quantity of blood 458 that approximates the volume that can be concentrated (dewatered) by the gel beads is introduced into the blood reservoir 416 through the inlet opening 442 and distribution tube 444. The blood 458 can be introduced through the needle of the original sample syringe or another device. The blood is shown after is has settled in the bottom of the blood reservoir 416.

In FIG. 25, the motor 384 is energized to rotate the separator and concentrator assembly 378 at a fast spin rate that effects centrifugal separation of the more dense erythrocytes in the blood from the PRP. The central tube 360 and attached rake 440 remain stationary during this rapid rotation, and the gel beads 460 are spun by the rotary components and held by the centrifugal force against the screen 430, beyond the reach of the tips 452 of the stationary rake tips 440. The centrifugal force causes the blood 458 to flow up the tapered inside wall 418 of the blood reservoir 416 and over the tip edge 449, to collect against the depth filter 424 as shown in FIG. 25. The separation is achieved as a function of cell density, sending the most dense erythrocytes outward and through the passageways of the depth filter 424. The platelets remain in the PRP layer 462 that forms against the depth filter 424.

After separation of the cells is complete, the rotation of the separator and concentrator assembly 378 is slowed. PRP flow passageways 451 lead from the outer separator chamber 453 to the concentrator basket 429. The PRP 462 flows from the pores and surface of the depth filter 424 downward through the PRP flow passageway 451 into the concentrating basket 429. Erythrocytes remain trapped in the pores and passageways of the depth filter 424 so that the PRP 463 reaching the basket 429 is substantially free of erythrocytes.

As shown in FIG. 26, the PRP 463 flows into contact with the desiccated gel beads 460 that have collected on the base 432 of the concentrating basket 429. As the beads absorb water from the PRP, they swell, and the PRP immediately adjacent the bead surface thickens and becomes tacky. The continuing slow movement of the concentration basket 429 past the stationary rake 440 and the vertical supports 434 stirs the beads 460, reducing gel polarization on the bead surface, and breaking up the bead clumps. This slow stirring movement of the rotary components is continued until the water removal stage is completed.

The motor speed is then increased to a fast spin mode, and the centrifugal force moves the gel beads 460 to the surface of the screen 430. The centrifugal force generated by the spin caused the PRP concentrate 464 to flow away from the surfaces of the beads and through the screen 430 to collect the PRP concentrate in the PRP reservoir as shown in FIG. 27. The PRP concentrate is removed with a syringe through tube 398 and PRP outlet port 360.

Figure 28:
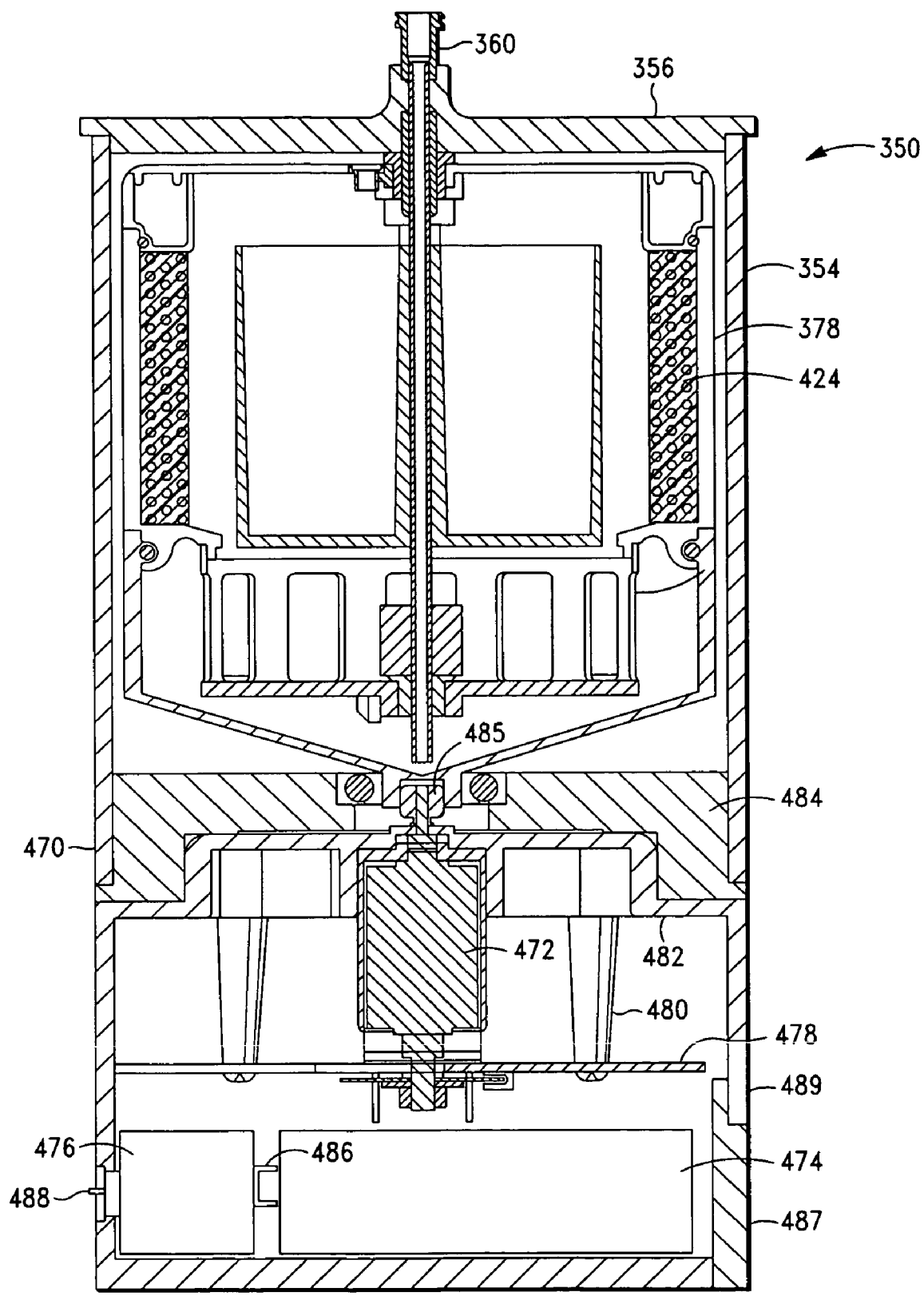
FIG. 28 is a cross-sectional view of a portable embodiment of this invention.

FIG. 28 is a cross-sectional view of a portable embodiment of this invention. This embodiment includes a blood separation and concentration system in the upper housing 354 that is identical to the blood separation and concentration system described with respect to FIGS. 19-23. Because these components are identical and to avoid unnecessary redundancy, no separate description of the identical components is provided herein, the description of these elements with respect to FIGS. 19-27 being incorporated by reference. For details about the blood separation and concentration systems, see the description of the components provided hereinabove with respect to FIGS. 19-23.

The system shown in FIGS. 19-23 comprises a disposable blood separation and concentration unit and a permanent motor control unit. This assembly is optimum of use in a laboratory or surgical setting found in a hospital or medical clinic.

For applications where a permanent motor and control system powered from conventional power sources is not practical, a portable fully integrated embodiment of this invention is provided. The major difference between the embodiment shown in FIG. 24 is the integration of the motor, power supply and control system in a unitary system with the blood separation and concentration system. The lower casing or housing 470 encloses the motor 472, power supply 474 and control system 476. The motor 472 is secured to a motor support plate 478 mounted on the motor support suspension 480. The motor support suspension 480 is secured the lower surface 482 of the base 484 in a position to maintain axial alignment of the motor with the axis of the rotary elements of the separator and concentrator unit. The motor drive shaft is secured to the separator and concentrator assembly by a coupling 485. The motor 472 is connected to the battery power supply 474 and control system 476 with conventional electrical circuitry (not shown). The battery power supply is electrically connected to the control system 476 with conventional electrical connections 486. A conventional removable plate 487 can be removably secured to the lower portion of the lower housing 489 in a position that permits insertion of the power supply battery 474 when it is removed. This allows insertion of an active battery immediately before deployment or use of the system.

The control system 476 is a conventional motor controller and timer that establishes and controls the motor speeds during the rapid rotation centrifugation phases of the blood separation and during the concentration stages, and during the slow rotation concentration stage. These stages are the same as are described hereinabove with respect to FIGS. 24-27.

The weight and size of the separator and concentrator elements are selected to conserve energy and to be fully operational with a standard 9 volt battery. This enables the device to be a completely portable system that does not require external power. It is thus suitable for use in mobile field units and field hospitals where self-powered, fully portable units are needed.

The operation of the embodiment shown in FIG. 28 is the same as is described above with respect to FIGS. 24-27.

The invention claimed is:

1. A portable, enclosed, disposable, self-contained, single-use PRP separator suitable for office use or emergency use for trauma victims, the portable separator comprising:

a single centrifugal separator unit having an integral erythrocyte separating volume;

a motor that is capable of separating erythrocytes from blood to produce PRP in less than 3 minutes with a total power consumption of less than 500 mAh by spinning the single centrifugal separator;

a container enclosing and sealingly containing both the single centrifugal separator unit and the motor; and an access port through the container operable to allow access to a central depression in the single centrifugal separator unit;

wherein the single centrifugal separator unit has a centrifugal drum having an inner wall surface with an upper edge and a lower edge, a drum bottom, and a central axis, the drum bottom defining the central depression and a floor sloping downward from the lower edge to the central depression;

wherein the inner wall surface of the centrifugal drum is sloped outwardly from the drum bottom at an angle of from 1° to 15° from the central axis;

wherein the single centrifugal separator unit consists essentially of the centrifugal drum and an outer annular erythrocyte capture chamber;

wherein the upper edge of the centrifugal drum is surrounded by the outer, annular erythrocyte capture chamber, the erythrocyte capture chamber including an inner wall that contacts or is shared with the centrifugal drum, an outer wall, and a lower wall, the outer wall having a top edge with an elevation higher than the inner wall, a capture volume of the erythrocyte capture chamber being the volume below the top of the inner wall, the capture volume being sized to retain the total volume of separated erythrocytes in the blood, whereby erythrocytes moving outward through the plasma during centrifugation flow are retained against the outer wall of the erythrocyte capture chamber during centrifugation and collect in the capture volume of the erythrocyte capture chamber when centrifugation is ended;

wherein the motor has a drive axis connected to the single centrifugal separator unit, the motor having the capacity to rotate the single centrifugal separator unit at a speed of at least 2,000 rpm for 120 seconds.

2. The portable separator of claim 1 including a battery connected to the motor through a switch, the battery having the capacity to provide power of at least 500 mAh to the motor.

3. The portable separator of claim 1, further comprising:
an access tube connected to and extending downward from a sterile syringe port;
wherein the container has a sterile vent and the sterile syringe port aligned with the central depression.

4. The portable separator of claim 1 wherein the inner wall of the erythrocyte capture chamber includes an upper portion having a slope forming an angle "a" of at least 25° relative to the central axis, the slope facilitating flow of platelets in the PRP flowing up and over the upper edge of the erythrocyte capture chamber during centrifugation.

5. A combination comprising:
a portable separator assembly operable to separate erythrocytes from a whole blood sample, having:
a centrifugal separator unit, and a motor that are capable of separating erythrocytes from blood to produce platelet-rich-plasma (PRP) in less than 3 minutes with a total power consumption of less than 500 mAh;
a) the centrifugal separator unit consisting essentially of a centrifugal drum and an outer annular erythrocyte capture chamber:
1. the centrifugal drum having a wall with an inner wall surface with an upper edge and a lower edge, a drum bottom, and a central axis, the drum bottom defining a floor sloping downward from the lower edge, and
2. the upper annular erythrocyte capture chamber having a first wall contacting or shared with the centrifugal drum wall, a bottom wall at a position between the upper and lower edge, and an outer wall defining an erythrocyte capture region;
b) a battery operable to provide about 500 mAh; and
c) the motor having a drive axis connected to the centrifugal separator unit, the motor having the capacity to rotate the centrifugal drum at a speed of at least 2,000 rpm for 120 seconds; and a plasma concentrating syringe separate from and operable to cooperate with the centrifugal separator unit, the syringe having a Luer fitting for connection to an access tube that extends to the bottom of the centrifugal drum to draw out a volume of the PRP from the centrifugal drum and concentrate the separated PRP.

6. The combination of claim 5 wherein the plasma concentrating syringe comprises a cylindrical barrel with an inner surface and an inlet/outlet port, a cylindrical actuated piston having an outer surface engaging the inner surface of the barrel, concentrating desiccated hydrogel beads positioned between the piston and the inlet/outlet port, and a filter positioned adjacent the inlet/outlet port to prevent escape of the concentrating desiccated hydrogel beads through the inlet/out port, whereby movement of the piston in a direction away from the inlet/outlet port draws PRP into the concentrating chamber, water is removed from the PRP by the concentrating desiccated hydrogel beads, thereby concentrating the PRP without activating the platelets or denaturing the fibrinogen in the plasma, and movement of the piston toward the inlet/outlet port expels concentrated PRP through the inlet/outlet port.

7. A portable, enclosed, disposable, self-contained, single-use platelet-rich-plasma PRP from whole blood separator suitable for office use or emergency use for trauma victims, the portable separator comprising:

a single isolated centrifugal separator unit consisting essentially of a single drum and an outer chamber,
the single drum having an annular wall extending from a first end to a second end, where at the second end a bottom wall slants to a central depression near a central axis of the single drum and an inner surface of the annular wall slopes outward away from the central axis, and
the outer chamber having a substantially U-shaped or V-shaped cross section defined by a first wall spaced a distance from the annular wall of the single drum, a second wall contacting or shared with the annular wall of the single drum and a bottom wall contacting both the first wall and the second wall,
wherein a void is not present between the annular wall of the single drum and second wall of the outer chamber and all portions of the whole blood are contained only within the single drum and outer chamber,
wherein the bottom wall is nearer the first end than the second end of the single drum;

a motor capable of spinning the single isolated centrifugal separator unit to separate erythrocytes from the whole blood to produce the PRP;

a drive axle interconnecting the single isolated centrifugal separator unit and the motor, wherein the motor drives the drive axle and the single isolated centrifugal separator unit to at least 1200 rpm for less than 3 minutes with a total power consumption of less than 500 mAh;

a battery operable to provide the 500 mAh to the motor;

a container to sealingly contain all of the single centrifugal separator unit, the motor, and the battery;

an access port through the container operable to allow access to the central depression in the single drum of the single centrifugal separator unit; and a separate isolated plasma concentrating syringe having:

a cylindrical barrel with an inner surface and an inlet/outlet port operable to cooperate with the access port to withdraw PRP from the central depression, a cylindrical piston having an outer surface engaging the inner surface of the barrel, concentrating desiccated hydrogel beads positioned between the piston and the inlet/outlet port, and a filter positioned adjacent the inlet/outlet port to prevent escape of the concentrating desiccated hydrogel beads through the inlet/outlet port, wherein movement of the piston in a direction away from the inlet/outlet port draws the material into the concentrating chamber to allow water to be removed from the PRP by the concentrating desiccated hydrogel beads and movement of the piston toward the inlet/outlet port expels concentrated PRP through the inlet/outlet port;

wherein concentrating the PRP occurs without activating the platelets or denaturing the fibrinogen in the PRP.

8. The portable separator of claim 7, wherein the access port is operable to allow introduction of a whole blood sample to fill the single drum with the whole blood for separation of the erythrocytes from plasma.

9. The portable separator of claim 7, wherein the inner wall surface of the single drum includes an angle of 1° to 15° relative to the central axis.

10. The portable separator of claim 9, wherein the first wall has a first top edge with an elevation higher than a second top edge of the second wall, wherein the volume of the outer chamber is the volume below the second top edge of the second wall;

wherein the volume is sized to retain the total volume of separated erythrocytes from the whole blood placed in the single centrifugal separator unit;

wherein erythrocytes moving outward through plasma of the whole blood during centrifugation flow are retained against the first wall of the outer chamber during centrifugation and collect in the lower volume of the outer chamber when centrifugation is ended.

11. The portable separator of claim 10 wherein the outer chamber includes an upper wall extending at a downward slope having an angle at least 25°, relative to the central axis, from the second wall of the outer chamber to the first wall of the second chamber.

12. The portable separator of claim 11, further comprising:

a cap operable to seal the single centrifugal separator unit within and separate from the container, but allow transfer of a selected material from the single drum to the outer chamber during centrifugation.

* * * * *